United States Patent
Phanstiel, IV et al.

(10) Patent No.: US 9,629,822 B2
(45) Date of Patent: Apr. 25, 2017

(54) FLAVONOID BASED ANTIVIRAL TARGETS

(71) Applicants: UNIVERSITY OF CENTRAL FLORIDA RESEARCH FOUNDATION, INC., Orlando, FL (US); FRIEDRICH ALEXANDER UNIVERSITY, Erlangen (DE)

(72) Inventors: Otto Phanstiel, IV, Oviedo, FL (US); Nuska Tschammer, Erlangen (DE)

(73) Assignees: University of Central Florida Research Foundation, Inc., Orlando, FL (US); Friedrich Alexander University, Erlangen (DE)

( * ) Notice: Subject to any disclaimer, the term of this patent is extended or adjusted under 35 U.S.C. 154(b) by 0 days.

(21) Appl. No.: 14/429,481

(22) PCT Filed: Sep. 23, 2013

(86) PCT No.: PCT/US2013/061172
§ 371 (c)(1),
(2) Date: Mar. 19, 2015

(87) PCT Pub. No.: WO2014/047551
PCT Pub. Date: Mar. 27, 2014

(65) Prior Publication Data
US 2015/0209323 A1 Jul. 30, 2015

Related U.S. Application Data

(60) Provisional application No. 61/704,074, filed on Sep. 21, 2012.

(51) Int. Cl.
*A61K 31/353* (2006.01)
*A61K 31/352* (2006.01)
*A61K 31/12* (2006.01)

(52) U.S. Cl.
CPC ............ *A61K 31/353* (2013.01); *A61K 31/12* (2013.01); *A61K 31/352* (2013.01)

(58) Field of Classification Search
None
See application file for complete search history.

(56) References Cited

U.S. PATENT DOCUMENTS 6,046,231 A 4/2000 Kosmeder, II et al.
2003/0065039 A1 4/2003 Kharazmi et al.
2009/0124688 A1 5/2009 Lin et al.

FOREIGN PATENT DOCUMENTS

EP 0872903 B1 10/2001
WO 03057210 A1 7/2003

OTHER PUBLICATIONS

Database CAPLUS Chemical Abstracts Service, Columbus, Ohio, US; Database Accession No. 1919:7006, Abstract of Tambor et al., Helvetica Chimica Acta (1919), 2, 101-11.*

(Continued)

*Primary Examiner* — Karl J Puttlitz
(74) *Attorney, Agent, or Firm* — Timothy H. Van Dyke; Beusse, Wolter, Sanks & Maire PLLC

(57) ABSTRACT

The present invention relates to novel compounds for modulating US28 receptor activity and methods for their use in preventing or treating US28 receptor-mediated disorders or conditions.

19 Claims, 5 Drawing Sheets

1: Xanthohumol

2: Butein

3: Baicalein: $R_1$=OH; $R_2$, $R_3$, $R_4$= H
4: Quercetin: $R_1$=H; $R_2$, $R_3$, $R_4$= OH 5a: VUF2274

5b: dihydroisoquinolinones

5c: tetrahydroisoquinolines

5d: S-(-)-IBMZ

(56) References Cited

OTHER PUBLICATIONS

Database CAPLUS Chemical Abstracts Service, Columbus, Ohio, US; Database Accession No. 1964:476442, Abstract of Mathai et al., Journal of the Indian Chemical Society (1964), 41(5), 347-51.*
Database Caplus Chemical Abstracts Service, Columbus, Ohio, US; Database Accession No. 1950:20071, Abstract of Vandrewalla et al., Proceedings—Indian Academy of Sciences, Section A (1948), 28A, 125-31.*
Database CAPLUS Chemical Abstracts Service, Columbus, Ohio, US; Database Accession No. 2012:273713, Abstract of Thornton et al., Current Organic Chemistry (2012), 16(1), 121-126.*
Dimmock, J. R. et al., "Bioactivities of chalcones", Curr Med Chem ,1999, vol. 6, pp. 1125-1149.
Sahu, N.K. et al., "Exploring Pharmacological Significance of Chalcone Scaffold: A Review", Curr. Med. Chem.,2012, vol. 19, pp. 209-225.
Lin, Y. M. et al., "Chalcones and Flavonoids as Anti-Tuberculosis Agents", Bioorg Med Chem, 2002, vol. 10, pp. 2795-2802.
Babu, M. A. et al., "Development of 3D-QSAR Models for 5-Lipoxygenase Antagonists: Chalcones", Bioorg Med Chem, 2002, vol. 10, pp. 4035-4041.
Sogawa, S. et al., "3,4-Dihydroxychalcones as Potent 5-Lipoxygenase and Cyclooxygenase Inhibitors", J Med Chem, 1993, vol. 36, pp. 3904-3909.
Zhao, F.et al., "Synthesis and Protein Tyrosine Phosphatase 1B-Inhibitory Activity of Chalcones", Asian J Chem, 2011, vol. 23, pp. 5339-5342.
Buckwold, V. et al., "Antiviral activity of hop constituents against a series of DNA and RNA viruses", Antiviral Res, 2004, vol. 61, pp. 57-62.
Wang, Y. et al., "Xanthohumol, a Prenylated Chalcone Derived from Hops, Suppresses Cancer Cell Invasion through Inhibiting the Expression of CXCR4 Chemokine Receptor", Curr Mol Med, 2012, vol. 12, pp. 153-162.
Chua, A. W.et al., "Butein downregulates chemokine receptor CXCR4 expression and function through suppression of NF-kappaB activation in breast and pancreatic tumor cells", Biochem Pharmacol, 2010, vol. 80, pp. 1553-1562.
Evers, D. et al., "Human cytomegalovirus-inhibitory flavonoids: Studies on antiviral activity and mechanism of action", Antiviral Research, 2005, vol. 68, pp. 124-134.
Kim, HJ. et al., "A new flavonol glycoside gallate ester from Acer okamotoanum and its inhibitory activity against human immunodeficiency virus-1 (HIV-10 integrase", J Nat Prod., 1998, vol. 61, pp. 145-148.
Hachet-Haas, M. et al., "Small neutralizing molecules to inhibit actions of the chemokine CXCL12", J Biol Chem, 2008, vol. 283, pp. 23189-23199.
Gao, J. L. et al., "Human Cytomegalovirus Open Reading Frame US28 Encodes a Functional Beta Chemokine Receptor", J Biol Chem, 1994, vol. 269, pp. 28539-28542.
Kralj, A. et al., "Identification of novel allosteric modulators for the G-protein coupled US28 receptor of human cytomegalovirus", Bioorg Med Chem Lett, 2011, vol. 21, pp. 5446-5450.
Boomker, J. M. et al., "US28 actions in HCMV infection: lessons from a versatile hijacker" Rev Med Virol, 2005, vol. 15, pp. 269-282.
Sodhi, A. et al., "Viral hijacking of G-protein-coupled-receptor signalling networks", Nat Rev Mol Cell Biol, 2004, vol. 5, pp. 998-1012.
Maussang, D. et al., "Herpesvirus-encoded G protein-coupled receptors as modulators of cellular function", Mol Pharmacol, 2009, vol. 76, pp. 692-701.
Vomaske, J. et al., "Human Cytomegalovirus US28: A Functionally Selective Chemokine Binding Receptor", Infect Disord Drug Targets, 2009, vol. 9, pp. 548-556.
Maussang, D. et al., "Human cytomegalovirus-encoded chemokine receptor US28 promotes tumorigenesis", Proc Natl Acad Sci U S A, 2006, vol. 103, pp. 13068-13073.
Tschammer, N. "Virally Encoded G protein-Coupled Receptors: Overlooked Therapeutic Opportunities?", Annual Reports in Medicinal Chemistry, 2012, vol. 47, pp. 379-392.
Jeffrey A. Smith, et al., "Structural basis for the activity of the RSK-specific inhibitor, SL0101", Bioorganic & Medicinal Chemistry, 2007, vol. 15, pp. 5018-5034.
Kazuaki Yamasaki et al., "Study of Kaempferol Glycoside as an Insulin Mimic Reveals Glycon to be the Key Active Structure", ACS Med. Chem. Lett., 2011, vol. 2, pp. 17-21.
Chimenti, J.A. "A new series of flavones, thioflavones, and flavanones as selective monoamine oxidase-B inhibitors", Bioorganic & Medicinal Chemistry, 2010, vol. 18, pp. 1273-1279.
PathDetect in Vivo Signal Transduction Pathway trans-Reporting Systems, Instruction Manual, Agilent Technologies, Inc., 2011; 219000-12, Revision B.
Bright-GloTM Luciferase Assay System, Technical Manual, Promega Corporation, Madison, WI, Sep. 2011; Part# TM052.
Phanstiel IV, O. et al., "Structure-activity investigations of polyamine-anthracene conjugates and their uptake via the polyamine transporter", Amino Acids, 2007, vol. 33, pp. 305-313.
Parisini, E. et al., "Halogen bonding in halo-carbon-protein complexes: a structural survey", Chem. Soc. Rev., 2011, vol. 40, pp. 2267-2278.
Hesselgesser, J. et al., "Identification and Characterization of Small Molecule Functional Antagonists of the CCR1 Chemokine Receptor", J Biol Chem, 1998, vol. 273, pp. 15687-15692.
Vischer, H. F. et al., "Identification of novel allosteric nonpeptidergic inhibitors of the human cytomegalovirus-encoded chemokine receptor US28", Bioorg Med Chem, 2010, vol. 18, pp. 675-688.
Casarosa, P. et al., "Identification of the first nonpeptidergic inverse agonist for a constitutively active viral-encoded G protein-coupled receptor", J Biol Chem, 2003, vol. 278, pp. 5172-5178.
Chan, K.F. et al., "Flavonoid Dimers as Bivalent modulators for P-Glycoprotein-Based Multidrug Resistance: Structure-Activity Relationships", Chem Med Chem, 2009, vol. 4, pp. 594-614.
Murata, T. et al., "Synthesis and structure-activity relationships of novel IKK-$\beta$ inhibitors. Part 3: Orally active anti-inflammatory agents", Bioorg. Med. Chem. Lett., 2004, vol. 14, pp. 4019-4022.
Pinto, D.G. et al., "Synthesis of 3-(2-benzyloxy-6-hydroxyphenyl)-1-methylpyrazoles by the reaction of chromones with methylhydrazine", J. Heterocycl. Chem., 2000, vol. 37, pp. 1629-1634.
Sang-Hun Jung, et al., "Structural requirement of isoflavonones for the inhibitory activity of interleukin-5", Eur. J. Med. Chem., 2003, vol. 38, pp. 537-545.
Owen, Sherry M., et al., RC-101, Retrocyclin-1 Analogue with Enhanced Activity against Primary HIV Type 1 Isolates, AIDS Research and Human Retroviruses, 2004, vol. 20:11, pp. 1157-1665.
Cole, Am., et al., "HIV-1 Adapts to a Retrocyclin with Cationic Amino Acid Substitutions That Reduce Fusion Efficiency of gp41", Journal of Immunology, 2006, vol. 176, pp. 6900-6905.
Kralj, A. et al., "Development of flavonoid-based inverse agonists of the key signaling receptor US28 of human cytomegalovirus", Journal of Medicinal Chemistry, Jun. 14, 2013, vol. 56, pp. 5019-5032.

* cited by examiner

FLAVONOID BASED ANTIVIRAL TARGETS

CROSS-REFERENCE TO RELATED APPLICATIONS

This application claims benefit under 35 USC 119 of the Sep. 21, 2013 filing date of U.S. Provisional Application No. 61/704,074, which is incorporated by reference herein.

BACKGROUND

Flavonoids are abundant in edible plants and possess a wide variety of biological activities, including antioxidant, anti-carcinogenic, antibacterial, anti-fungal activities, and also may play a role in preventing infectious diseases.[1,2] One class of flavonoids, the chalcones, are known to inhibit enzymes such as 15-hydroxy-prostaglandin dehydrogenase[1a], 5-lipoxygenase[3], cyclooxygenase[4] and protein tyrosine phosphatase 1B[5]. Thus, chalcone-based drugs are potential tools for the treatment of gastric lesions', asthma, inflammation and allergies[4], as well as type 2 diabetes and obesity[5].

In 2004, xanthohumol 1 (shown in FIG. 1), a prenylated chalcone derived from hops, showed moderate antiviral activity against several herpes viruses, including human cytomegalovirus (HCMV).[6] In addition to viral signaling, inhibitors of pro-growth signaling cascades could also have applications in human cancer. For example, xanthohumol and butein 2 (a related tetrahydroxychalcone shown in FIG. 1) downregulate the CXCR4 chemokine receptor and inhibit tumor growth.[7,8] Another related chalcone flavonoid, isoliquiritigenin, which was shown to inhibit the growth of prostate cancer cells, induce cell cycle arrest and apoptosis in lung cancer cells and exhibit anti-estrogenic activity towards breast cancer cells.[9]

Chemokine receptors are heptahelical G protein-coupled receptors (GPCRs) that bind chemokines (i.e., small chemotactic cytokines, critical for recruiting and activating cells of the immune system during inflammation). Butein 2 prevents interaction between the CXCR4 chemokine receptor and its endogenous ligand chemokine CXCL12, which has been shown to mediate human immunodeficiency virus-induced neurotoxicity, proliferative retinopathy and chronic inflammation.[10] Butein prevents binding of CXCL12 to both its receptors, CXCR7 and CXCR4, but does not prevent the binding of other CXCR4 ligands, like CCL5 and CXCL8, to their receptor. These observations suggest that this chalcone may actually bind to the CXCL12 chemokine rather than its receptor, CXCR4.[10]

The US28 receptor is one of the viral G-protein coupled receptors (vGPCRs) encoded in double stranded DNA of Human Cytomegalovirus (HCMV). It possesses high homology with human chemokine receptors. For example, US28 has 30% and 28% amino acid sequence homology with the human CCR1 and CXCR3 receptor, respectively.[11] This similarity enables efficient coupling to signaling networks of the infected host.[12] The US28 receptor possesses the ability to bind different human CC-chemokines (including CCL5/Rantes), as well as the CX3C-chemokine CX3CL1/Fractalkine. Similar to other vGPCRs, the US28 receptor is also characterized by ligand-independent signaling. In fact, US28 constitutive signaling enables virus survival, host invasion and, in some cases, oncogenesis or cardiovascular disease, by exploiting preferred signaling cascades.[13] HCMV establishes a lifelong persistent/latent infection in immuno-competent hosts and can lead to severe and life-threatening diseases in patients with immature or suppressed immune systems.[14,15] Thus, the US28 receptor may play a role in viral dissemination and persistence, as well as a role in cardiovascular disease and tumorigenesis.[15,16]

Recent studies have looked at the specific mechanism of action of the following two flavonoids on viral properties such as transcription factor activation, receptor tyrosine kinase activity, and nuclear translocation. Baicalein 3 has been shown to have activity against HCMV by preventing viral entry. This is accomplished by targeting the kinase activity of EGFR, which is required for HCMV entry and cellular activation.[17] Quercetin 5, on the other hand, was shown to inhibit HIV-1 integrase, which mediates the insertion of viral DNA into host cellular DNA. Quercetin is also essential for viral replication and virion production.[18] To date, some chalcones and flavonoids have been assessed for their ability to interact with the US28 receptor, but their efficacy needs improvement prior in vivo usage. Compounds 5a-d represent the other known US-28 receptor inverse agonists which are not predicated upon flavones architectures.

DETAILED DESCRIPTION

Figure 1:
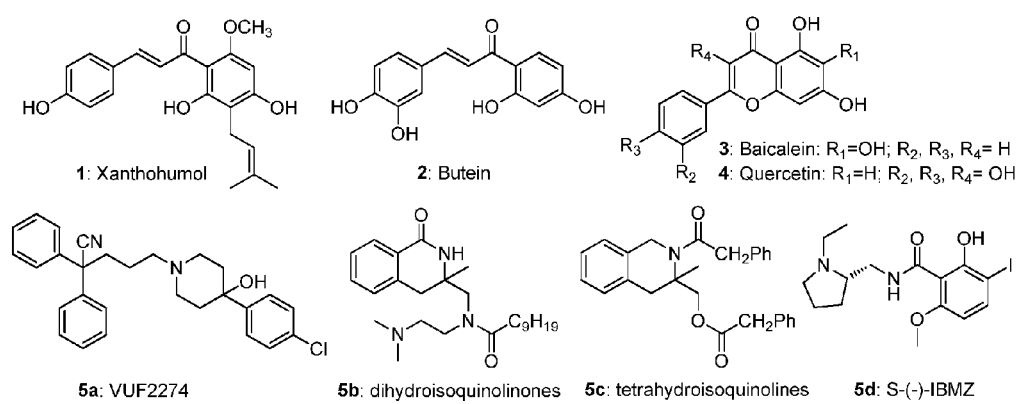
FIG. 1 shows the structures of bioactive chalcones and flavones 1-4 and known inverse agonists 5a-5d.

The present invention is directed to novel compounds and compositions having US28 receptor modulating properties. In certain embodiments, the compounds are inverse agonists of the US28 receptor in a subject. As mentioned above, US28 constitutive signaling enables virus survival, host invasion, and, in some cases, oncogenesis or cardiovascular disease, by exploiting preferred signaling cascades. The compositions may be utilized for treating a subject suffering from or diagnosed with a disease, disorder, and/or medical condition (collectively "disorder") mediated at least in part by US28 receptor activity. The disorder may be a virus, cardiovascular disease, chronic inflammation, or cancer, for example. When the disorder is a virus, the US28 receptor modulator is believed to inhibit virus replication to at least a degree. In a particular embodiment, the disorder may be a herpes virus, such as Human Cytomegalovirus (HCMV). The US28 receptor is a key viral receptor used in proliferation of the HCMV virus. Thus, a US28 receptor modulator, such as those described herein, should block the ability of the HCMV virus to proliferate, even in already infected cells. In another embodiment, the US28 receptor modulator may be administered to inhibit the proliferation of Human immunodeficiency virus (HIV). When the virus is one other than HCMV, the flavonoid derivative may be affecting a related receptor important for viral entry and/or proliferation. When this disorder is cancer, the flavonoid derivative may be affecting a related receptor important involved in MAPK signaling.

In one aspect, there is provided a composition comprising a compound selected from the group consisting of 8a-8j, 9a-9j, 11a-11d, 12a-12b, 13a, and 13h, or an analog, derivative, prodrug, stereoisomer, or pharmaceutically acceptable salt thereof. In an embodiment, the compound is selected from the group consisting of 8l, 8m, 9c, 9g, 9h, and 9i; or an analog, derivative, prodrug, stereoisomer, or pharmaceutically acceptable salt thereof. In another embodiment, the compound is selected from the group consisting of 8f, 8g, 8i, 8m, and 11b, or an analog, derivative, prodrug, stereoisomer, or pharmaceutically acceptable salt thereof. In a particular embodiment, the compound comprises 11b, or an analog, derivative, prodrug, stereoisomer, or pharmaceutically acceptable salt thereof, which was found to be a full inverse agonist of US28 receptor signaling and not toxic.

In another aspect, there is provided a US28 receptor modulator comprising a compound selected from the group consisting of 8a-8j, 9a-9j, 11a-11d, 12a-12b, 13a, and 13h, or an analog, derivative, prodrug, stereoisomer, or pharmaceutically acceptable salt thereof. In an embodiment, the compound is selected from the group consisting of 8l, 8m, 9c, 9g, 9h, and 9i, or an analog, derivative, prodrug, stereoisomer, or pharmaceutically acceptable salt thereof. In another embodiment, the compound is selected from the group consisting of 8f, 8g, 8i, 8m, and 11b, or an analog, derivative, prodrug, stereoisomer, or pharmaceutically acceptable salt thereof.

In another aspect, there is provided a composition comprising 5-(Benzyloxy)-2-(5-bromo-2-methoxyphenyl)-4H-chromen-4-one (11b) or an analog, derivative, prodrug, stereoisomer, or pharmaceutically acceptable salt thereof.

In another aspect, there is provided a composition comprising a compound of the following structure:

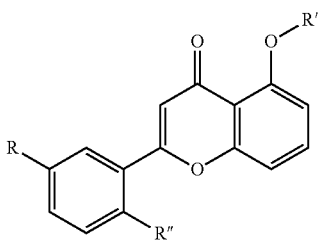

wherein R=a halogen (such as fluoro, chloro, bromo or iodo).
wherein R'=a lipophilic group; and
wherein R"=O-alkyl, N-alkyl or alkyl;
or an analog, derivative, prodrug, stereoisomer, or pharmaceutically acceptable salt thereof.

In an embodiment, the lipophilic group (R') comprises a C1-C22 alkyl group, including branched or unbranched saturated hydrocarbon compounds, such as methyl, ethyl, propyl, isopropyl, butyl, isobutyl, sec-butyl, pentyl, isopentyl, hexyl, and the like, or an alkenyl group like allyl, or isopentenyl, or a cyclic lipophilic group (e.g., cycloalkyl like cyclohexyl or cyclopropylmethyl, cyclobutylmethyl, cyclopentylmethyl, cyclohexylmethyl, substituted benzyl or substituted naphthylmethyl) or hydrogen. These side chains can also contain additional functional groups to improve their binding affinity to the US28 receptor like alkoxy, hydroxy, amino or carbonyl groups.

The R" group comprises O-alkyl, N-alkyl or alkyl substituents, where the alkyl group comprises a C1-C22 alkyl group, including but not limited to branched or unbranched saturated hydrocarbon compounds (such as methyl, ethyl, propyl, isopropyl, butyl, isobutyl, sec-butyl, pentyl, isopentyl, hexyl, and the like); an alkenyl group (such as allyl, or isopentenyl); a cyclic lipophilic group (e.g., cycloalkyl (such as cyclohexyl, cyclopropylmethyl, cyclobutylmethyl, cyclopentylmethyl, cyclohexylmethyl, substituted benzyl, or substituted naphthylmethyl)); or hydrogen. These side chains can also contain additional functional groups to improve their binding affinity to the US28 receptor such as alkoxy, hydroxy, amino or carbonyl groups with O-methyl, O-ethyl and O-propyl being preferred.

It is appreciated that any of the above compositions may be provided as a pharmaceutical composition with the inclusion of a pharmaceutically acceptable carrier. Further, in certain embodiments, it is contemplated that the compounds described herein (any one or more of the above compounds synthesized herein) may act as a modulator of the US28 receptor (US28 receptor modulator). In certain embodiments, the US28 receptor modulator defines an agonist of the US28 receptor. In other embodiments, the US28 receptor modulator defines a partial or full inverse agonist of the US28 receptor. In other embodiments, the US28 receptor modulator compounds described herein may act as an antagonist to the US28 receptor. In any case, the present invention contemplates the use of any one or more of the above compounds synthesized herein in the prevention or treatment of a disorder mediated by US28 receptor activity, such as: a related virus, including but not limited to HCMV; cancer; cardiovascular disease; and/or other disorders characterized by acute or chronic inflammation.

In another aspect, there is provided a method of inhibiting US28 receptor activity comprising administering an effective amount of a US28 receptor modulator as set forth herein effective to modulate US28 receptor activity. In one embodiment, the US28 receptor modulator comprises 5-(Benzyloxy)-2-(5-bromo-2-methoxyphenyl)-4H-chromen-4-one (11b) or an analog, derivative, prodrug, stereoisomer, or pharmaceutically acceptable salt thereof.

It is contemplated that the majority of the compounds are not chiral, and thus do not have stereoisomers associated with their structure, with the exception of saturated ring systems found in certain compounds. In such cases, stereoisomers could be made by appending a chiral side chain according to known methods. In certain embodiments, hydrogen atoms could be replaced by their deuterium isotope. For example, O-methyl groups could be replaced by $OCD_3$ groups with enhanced pharmaceutical effects. The present inventors note that systems comprising a bromo-substitutent and an O—R group have some conformational restrictions due to the high energy cost of rotating the ring containing these substituents through the plane of the molecule. This would lead to two conformationally locked rotational isomers at room temperature for some of these systems.

In another aspect, there is provided a method for preventing or treating a disorder associated with undesired US28 receptor activity in a subject comprising administering to the subject an effective amount of a US28 receptor modulator, which may be any compound set forth herein that modulates US receptor activity. In particular embodiments, one or more of the compounds described herein may be utilized in the prevention or treatment of a virus, including but not limited to HIV-1, HIV-2, or HCMV. In other embodiments, one or more of the compounds described herein may be utilized in the prevention or treatment of cancer; cardiovascular disease; and/or other disorders characterized by acute or chronic inflammation.

In another aspect, there is provided a method for treating or preventing a disorder mediated by US28 receptor activity in a subject in need comprising administering to the subject an effective amount of a US28 receptor modulator as described herein. In certain embodiments, the disorder comprises a virus, such as a herpes virus, whose proliferation is mediated at least in part by US28 receptor activity. In an embodiment, the herpes virus is a Herpes simplex virus, which is a viral disease from the herpesviridae family caused by both Herpes simplex virus type 1 (HSV-1) and type 2 (HSV-2). In an embodiment, the virus comprises human cytomegalovirus (HCMV) (human herpesvirus-5 (HHV-5)). In another embodiment, the virus comprises Human immunodeficiency virus (HIV). Evidence is provided here that these compounds are able to target non-HCMV viruses like HIV presumably via the compound's ability to target proteins in these other viruses and inhibit viral entry or proliferation. In another embodiment, the disorder comprises a bacterial infection. In still another embodiment, the disorder comprises a cancer characterized at least in part by tumorogenesis. In still another embodiment, the disorder comprises acute or chronic inflammation. In certain embodiments, the US28 receptor modulator is administered to a subject exhibiting symptoms of the disorder mediated by US28 receptor activity.

In another aspect, there is provided a method for treating or preventing a subject exhibiting a symptom of a disorder mediated at least in part by US28 receptor activity comprising administering to the subject an effective amount of a US28 receptor modulator as described herein.

In another aspect, there is provided a method for treating or preventing a human cytomegalovirus (HCMV) in a subject comprising administering to the subject an effective amount of a US28 receptor modulator as described herein.

In another aspect, there is provided a method for inhibiting the proliferation of HIV in a subject comprising administering to the subject an effective amount of a US28 receptor modulator as described herein.

1.1 DEFINITIONS

It is important to an understanding of the present invention to note that all technical and scientific terms used herein, unless defined herein, are intended to have the same meaning as commonly understood by one of ordinary skill in the art. The techniques employed herein are also those that are known to one of ordinary skill in the art, unless stated otherwise. Prior to setting forth the invention in detail and for purposes of more clearly facilitating an understanding the invention as disclosed and claimed herein, the following definitions are provided.

As used herein, the terms "about" and "approximately" as used herein refers to –values that are ±10% of the stated value.

As used herein, the terms "administering" or "administration" of a composition as described herein to a subject includes any route of introducing or delivering to a subject a compound to perform its intended function. The administering or administration can be carried out by any suitable route, including orally, intranasally, parenterally (intravenously, intramuscularly, intraperitoneally, or subcutaneously), rectally, or topically. Administering or administration includes self-administration and the administration by another.

As used herein, the term "alkyl" as used herein refers to a branched or unbranched saturated hydrocarbon groups typically although not necessarily containing 1 to about 22 carbon atoms, such as methyl, ethyl, n-propyl, isopropyl, n-butyl, isobutyl, t-butyl, pentyl, hexyl, heptyl octyl, decyl, and the like, as well as cycloalkyl groups such as cyclopropylmethyl, cyclobutylmethyl, cyclopentyl, cyclohexyl and the like. Reference to specific alkyl groups is meant to include all constitutional isomers that exist for that group. Generally, although again not necessarily, alkyl groups herein may contain 1 to about 22 carbon atoms. If not otherwise indicated, the terms "alkyl" includes linear, branched, cyclic, unsubstituted, substituted, and/or heteroatom-containing alkyl or lower alkyl, respectively. In addition, the term 'unsaturated' side chains include structures containing a carbon-carbon multiple bond like benzyl, allyl, isopentenyl, propargyl, or an alkenyl or alkynyl chain.

As used herein, the term "analog" refers to a compound having a structure similar to that of another one, but differing from it with respect to a certain component. The compound may differ in one or more atoms, functional groups, or substructures, which may be replaced with other atoms, groups, or substructures. In one aspect, such structures possess at least the same or a similar therapeutic efficacy.

As used herein, the term "anti-viral" or "anti-viral activity" refers to an agent or method that can inhibit and/or reduce the replication, infectivity, progress and/or emission of a virus, or that can reduce the likelihood that a person or animal exposed to potentially infective viral particles will contract the viral disease, regardless of which stage or step of the viral cycle or transmission process is inhibited.

As used herein, the term "cancer" refers to or describes the physiological condition in mammals that is typically characterized by unregulated cell growth or tumorigenesis. Exemplary cancers include lung cancer, bone cancer, liver cancer, pancreatic cancer, skin cancer, cancer of the head or neck, cutaneous or intraocular melanoma, uterine cancer, ovarian cancer, rectal cancer, cancer of the anal region, stomach cancer, colon cancer, breast cancer, uterine cancer, carcinoma of the sexual and reproductive organs, Hodgkin's Disease, cancer of the esophagus, cancer of the small intestine, cancer of the endocrine system, cancer of the thyroid gland, cancer of the parathyroid gland, cancer of the adrenal gland, sarcoma of soft tissue, cancer of the bladder, cancer of the kidney, renal cell carcinoma, carcinoma of the renal pelvis, neoplasms of the central nervous system (CNS), neuroectodermal cancer, spinal axis tumors, glioma, meningioma, and pituitary adenoma.

As used herein, the term "cardiovascular disease" refers any abnormal condition characterized by dysfunction of the heart and blood vessels. Cardiovascular disease includes but is not limited to atherosclerosis, cerebrovascular disease, and hypertension.

As used herein, "derivative" refers to a compound derived or obtained from another and containing essential elements of the parent compound. In one aspect, such a derivative possesses at least the same or similar therapeutic efficacy as the parent compound. Derivatives may include, but are not limited to, esters, enol ethers, enol esters, acetals, ketals, orthoesters, hemiacetals, hemiketals, solvates, hydrates, and metabolites of the base compound. A "metabolite" is a pharmacologically active product produced through metabolism in the body of a specified compound or salt thereof.

Such products can result, for example, from the oxidation, reduction, hydrolysis, amidation, deamidation, esterification, deesterification, enzymatic cleavage, and the like, of the administered compound.

As used herein, the term "disorder" includes any disease, disorder, medical condition or other abnormal physical state, including those related to or involving US28 receptor activity in the transmission, presence, and/or progression of the disorder. Such disorders are said to be "related to," "associated with," or mediated (at least in part) by US28 receptor activity.

As used herein, by the terms "effective amount," "amount effective," or the like, it is meant an amount effective at dosages and for periods of time necessary to achieve the desired result.

As used herein, the term "herpes virus" refers to any virus belonging to the family Herpesviridae, including the Human Cytomegalovirus (HCMV).

As used herein, the term "inverse agonist" or "US28 inverse agonist" refers to a compound as described herein that binds to the US28 receptor, but induces a pharmacological response opposite to that of a US28 receptor agonist.

As used herein, the term "antagonist" or "US28 antagonist" refers to a compound that binds to the US28 receptor to form a complex that does not give rise to any response, as if the receptor were unoccupied and has reduced signaling. Note; the US28 receptor is constituitively active and has baseline signaling without any chemokine bound. An antagonist inhibits the US28 receptor from binding with another ligand or reduces its downstream signaling.

As used herein, the term "partial inverse agonist" or a "partial antagonist" is a substance that provides a level of stimulation (inverse) or inhibition, respectively, to its binding partner that is not fully or completely inversely agonistic or antagonistic, respectively.

As used herein, the term "modulator" or "US28 receptor modulator" refers broadly to a compound having activity (directly or indirectly) as an agonist, antagonist or an inverse agonist to the US28 receptor. In certain embodiments, the modulator may enhance an inverse effect or inhibit US28 receptor binding and/or signaling in a statistically significant manner. The modulator may be a full inverse agonist, partial inverse agonist, or an antagonist of the US28 receptor. Since the US28 receptor has high sequence homology to other known cell receptors, a modulator may also bind and affect other proteins, especially G-coupled protein receptors.

As used herein, the term "mediated by" means at least in part mediated by. A disorder mediated by US28 receptor activity is one whose progression or proliferation is increased by US28 receptor activity. Since the US28 receptor has high sequence homology to other known cell receptors, these compounds may also bind and affect other proteins, especially G-coupled protein receptors.

As used herein, the term "pharmaceutically acceptable salt" refers to salts of the compounds described herein prepared from pharmaceutically acceptable non-toxic bases or acids, including inorganic or organic bases and inorganic or organic acids. Examples of salts derived from inorganic bases include aluminum, ammonium, calcium, copper, ferric, ferrous, lithium, magnesium, potassium, sodium, zinc, and the like. Particularly preferred are the ammonium, calcium, magnesium, potassium, and sodium salts. Salts derived from pharmaceutically acceptable organic non-toxic bases include salts of primary, secondary, and tertiary amines, substituted amines including naturally occurring substituted amines, cyclic amines, and basic ion exchange resins, such as arginine, betaine, caffeine, choline, N,N'-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, polyamines like putrescine, spermidine or spermine, as well as procaine, purines, theobromine, triethylamine, trimethylamine, tripropylamine, tromethamine, and the like.

As used herein, the terms "pharmaceutically acceptable carrier" or "physiologically acceptable carrier" as used herein refer to one or more formulation materials suitable for accomplishing or enhancing the successful delivery of the pharmaceutical composition prepared and delivered according to aspects of the invention.

As used herein, the term "preventing" means causing the clinical symptoms of the disorder state not to worsen or develop, e.g., inhibiting the onset of the disorder, in a subject that may be exposed to or predisposed to the disorder state, but does not yet experience or display symptoms of the disorder state.

As used herein, the term "prodrug" refers to a compound that is converted to a therapeutically active compound after administration, and the term should be interpreted as broadly herein as is generally understood in the art. Generally, but not necessarily, a prodrug is inactive or less active than the therapeutically active compound to which it is converted.

As used herein, the term "stereoisomer" refers to a compound which has the identical chemical constitution, but differs with regard to the arrangement of the atoms or groups in space.

As used herein, the term "subject" refers to any animal (e.g., a mammal), including, but not limited to, humans, which may be the recipient of a particular treatment.

As used herein, the terms "treating" or "treatment" or "alleviation" refers to both therapeutic treatment and prophylactic or preventative measures, wherein the objective is to prevent or slow down (lessen) the targeted pathologic condition or disorder.

As used herein, the term "US28" or "US28 receptor" refers to a constitutively active chemokine receptor encoded by CMV (cytomegalovirus), for example.

As used herein, the term "US28 receptor modulator" or "US28 receptor inhibitor" refers to a compound that selectively modulates activity of the US28 receptor, such as by preventing transduction of US28 receptor signal stimulated by a US28 receptor ligand. It is appreciated that the term US28 receptor modulator is not limited to a compound that can only modulate the US28 receptor. Since the US28 receptor has high sequence homology to other known cell receptors, it is possible that the US28 receptor modulators (compounds) described herein will also bind and affect other proteins, especially G-coupled protein receptors. These other proteins could be "non-US-28 receptors," or other receptors structurally similar to the US28 receptor.

1.2 SYNTHESIS

The following explanation details the synthesis of numerous US28 receptor modulators in accordance with an aspect of the present invention. The activity of the synthesized compounds towards the US28 receptor is shown in the following section.

To generate compounds 8a-8j and 9a-9j, specific carbonyl precursor compounds were necessary. While many of the required benzaldehydes and acetophenones were commercially available, several had to be made via O-alkylation of phenolic precursors 6a-c. As shown in Scheme 1, the desired alkyl groups were readily introduced in good yields.

Scheme 1$^a$

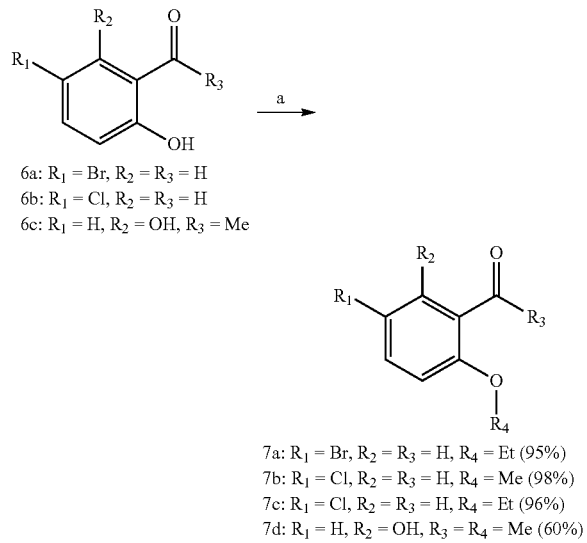

7a: $R_1$ = Br, $R_2$ = $R_3$ = H, $R_4$ = Et (95%)
7b: $R_1$ = Cl, $R_2$ = $R_3$ = H, $R_4$ = Me (98%)
7c: $R_1$ = Cl, $R_2$ = $R_3$ = H, $R_4$ = Et (96%)
7d: $R_1$ = H, $R_2$ = OH, $R_3$ = $R_4$ = Me (60%)

$^a$Reagents: a) MeI or EtBr, DMF, 2 days, rt

With the required carbonyl compounds in hand, a series of chalcones 8a-j and flavonols 9a-j were synthesized via Scheme 2 (below) in good yield. In general, the condensation of the respective methoxybenzaldehyde and acetophenone derivatives in strong base at 85° C. provided the desired chalcone target (8, Scheme 2).[20] These chalcone-producing reactions gave good yields and high purities after column chromatography. In the synthesis of 8a, prolonged reaction time (overnight stirring) resulted in the degradation of the product, byproduct formation, and lower yields (54%). Shorter reaction times (3 hours at reflux) were shown to be more optimal in terms of maximizing the yields of these chalcone systems. The reaction rates were system dependent, however, and the couplings could, in some cases, be conducted at 25° C.

In most cases, the pure product was rapidly obtained from the crude mixture by heating and sonicating the crude solid in hexane, followed by cooling the mixture to room temperature and filtering of the precipitated pure compound. Due to the simplicity of this workup, the yields were actually higher than the isolated yields listed in Scheme 2 as some of the chalcone product was also observed in the filtrate. The amount of product remaining in the filtrate varied depending upon the structure of the chalcone and the temperature at which the reaction was performed. Lower reaction temperatures typically gave less complex product mixtures. It was also observed that the co-distillation of many of the salicylaldehyde starting materials derivatives with aqueous alcohol solvents (MeOH, EtOH), which facilitated their removal during the workup concentration step. In cases where significant amounts of the byproducts were formed, substances were separated by column chromatography.

Conversion of chalcone 8 to the respective 3-hydroxy-4H-chromen-4-one derivative 9, was accomplished using 35% $H_2O_2$ in presence of strong base.[21] This reaction was performed using two conditions: first at 0° C. and then at room temperature. The ice bath condition resulted in low conversion as observed by TLC. The reaction was warmed to room temperature and demonstrated higher conversion to product. Subsequent addition of 1M HCl typically resulted in the formation of the desired product 9 as a white precipitate in moderate yield. Since HCl addition resulted in precipitation of the respective products 9a-j, they were each filtered to facilitate the workup and all but 9f were further purified by column chromatography. Conveniently, due to the poor solubility of 9f in chloroform, this substance was purified by filtration after boiling in chloroform and slow cooling to 4° C. (albeit in 28% yield). Overall, this approach provided rapid entry to this structure class for bioevaluation.

Scheme 2$^a$

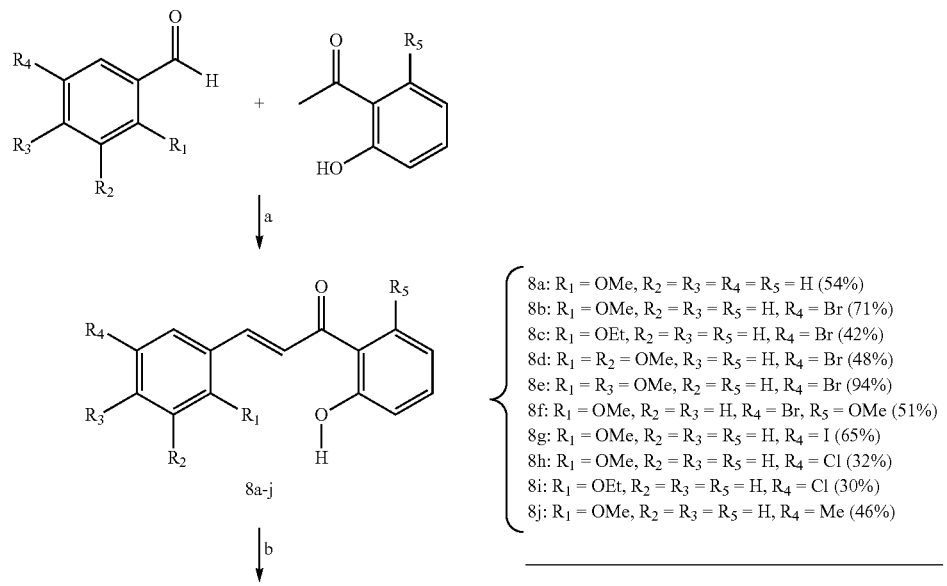

8a: $R_1$ = OMe, $R_2$ = $R_3$ = $R_4$ = $R_5$ = H (54%)
8b: $R_1$ = OMe, $R_2$ = $R_3$ = $R_5$ = H, $R_4$ = Br (71%)
8c: $R_1$ = OEt, $R_2$ = $R_3$ = $R_5$ = H, $R_4$ = Br (42%)
8d: $R_1$ = $R_2$ = OMe, $R_3$ = $R_5$ = H, $R_4$ = Br (48%)
8e: $R_1$ = $R_3$ = OMe, $R_2$ = $R_5$ = H, $R_4$ = Br (94%)
8f: $R_1$ = OMe, $R_2$ = $R_3$ = H, $R_4$ = Br, $R_5$ = OMe (51%)
8g: $R_1$ = OMe, $R_2$ = $R_3$ = $R_5$ = H, $R_4$ = I (65%)
8h: $R_1$ = OMe, $R_2$ = $R_3$ = $R_5$ = H, $R_4$ = Cl (32%)
8i: $R_1$ = OEt, $R_2$ = $R_3$ = $R_5$ = H, $R_4$ = Cl (30%)
8j: $R_1$ = OMe, $R_2$ = $R_3$ = $R_5$ = H, $R_4$ = Me (46%)

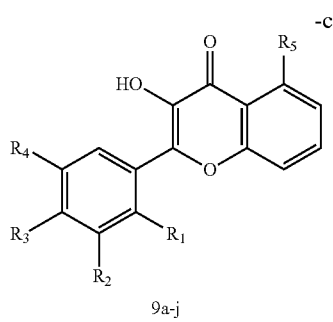

9a: $R_1$ = OMe, $R_2$ = $R_3$ = $R_4$ = $R_5$ = H (51%)
9b: $R_1$ = OMe, $R_2$ = $R_3$ = $R_5$ = H, $R_4$ = Br (80%)
9c: $R_1$ = OEt, $R_2$ = $R_3$ = $R_5$ = H, $R_4$ = Br (47%)
9d: $R_1$ = $R_2$ = OMe, $R_3$ = $R_5$ = H, $R_4$ = Br (39%)
9e: $R_1$ = $R_3$ = OMe, $R_2$ = $R_5$ = H, $R_4$ = Br (81%)
9f: $R_1$ = OMe, $R_2$ = $R_3$ = H, $R_4$ = Br, $R_5$ = OMe (28%)
9g: $R_1$ = OMe, $R_2$ = $R_3$ = $R_5$ = H, $R_4$ = I (44%)
9h: $R_1$ = OMe, $R_2$ = $R_3$ = $R_5$ = H, $R_4$ = Cl (49%)
9i: $R_1$ = OEt, $R_2$ = $R_3$ = $R_5$ = H, $R_4$ = Cl (60%)
9j: $R_1$ = OMe, $R_2$ = $R_3$ = $R_5$ = H, $R_4$ = Me (71%)

9a-j

[a]Reagents: a) 40% KOH/MeOH, 85° C.; b) 35% $H_2O_2$, KOH/96% EtOH, then 1M HCl Synthesis of the 5-hydroxy-4H-chromen-4-ones required a modified approach and is illustrated in Scheme 3. Since complex mixtures were generated during the direct condensation of dihydroxyacetophenone 10a and benzaldehyde, a protecting group strategy was employed. In this regard, the mono O-benzyl derivative 10b was synthesized from dihydroxyacetophenone, 10a using benzyl bromide and base in 58% yield. In subsequent steps, benzaldehyde derivatives 6d ($R_4$=H) and 6a ($R_4$=Br) reacted cleanly with ketone 10b (R=OBn) to provide chalcones 8k (60%) and 8l (82%), respectively. The synthesis of flavones 11a and 11b involved the ring closure of the respective chalcones 8 in presence of iodine and DMSO.[20] The reaction was completed in 3 hours and provided good yields for these systems and excellent purity after column chromatography.

The 5-hydroxy-4H-chromen-4-ones (12a and 12b in Scheme 3 (below)) were then obtained via debenzylation of 11a and 11b, respectively. The debenzylation was performed in acetic acid and water (4:1) ratio at 110° C. for 24 hours.[21] Along with the desired product (12), both benzyl alcohol and benzyl acetate were observed as byproducts of the acetolysis reaction. These could be removed by column chromatography to provide the respective derivatives 12a (67%) and 12b (70%) in high purity.

Scheme 3[a]

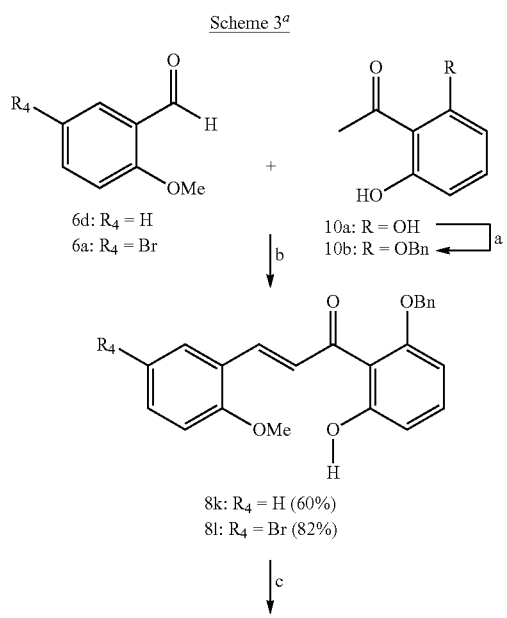

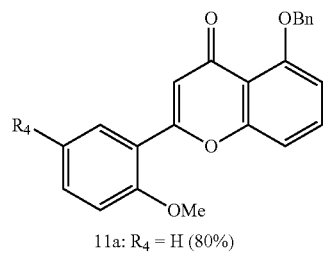

11a: $R_4$ = H (80%)
11b: $R_4$ = Br (55%)

↓d

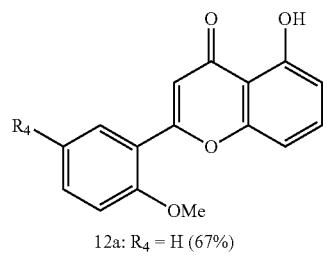

12a: $R_4$ = H (67%)
12b: $R_4$ = Br (70%)

[a]Reagents: a) Benzyl bromide, KI, $K_2CO_3$, acetone, reflux/$N_2$ atmosphere (58% yield); (b) 40% KOH/MeOH, 85° C.; (c) Iodine/DMSO, reflux at 140° C.; (d) $CH_3COOH$: $H_2O$ (Ratio of 4:1), 110° C.

As shown in Scheme 4 (below), 8a and 8b were converted to their 4H-chromen-4-one derivatives (11c and 11d) using iodine and DMSO at 140° C.[20] Compound 8b was also converted to the chroman-4-one derivative 13b (11%) using a week-long reflux in sodium acetate and n-BuOH.[22] It was observed that significant production of the related chroman-4-one 13h (R=Cl; 20% yield) during the synthesis of its precursor chalcone 8h in alcoholic KOH (Scheme 2). In this regard, some chalcone systems like 8h after 3 hours of reflux were partially converted to the chroman-4-one system during the chalcone synthesis step (presumably via an intramolecular Michael addition).

Scheme 4[a]

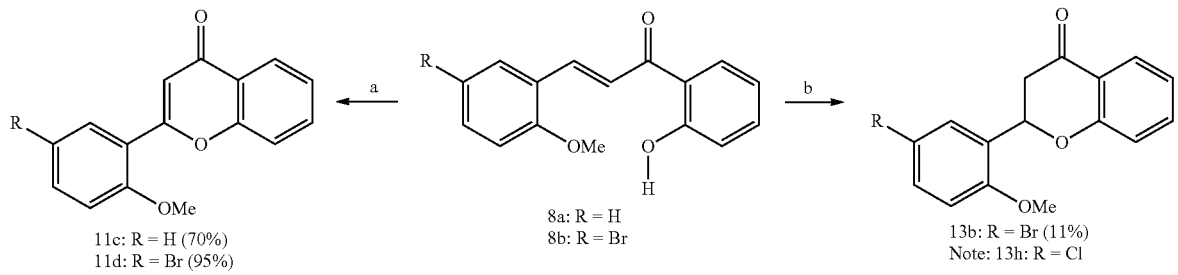

8a: R = H
8b: R = Br

11c: R = H (70%)
11d: R = Br (95%)

13b: R = Br (11%)
Note: 13h: R = Cl

[a]Reagents: a) Iodine/DMSO, 140° C.; b) CH3COONa, n-butanol, 118° C.

1-(1-Hydroxynaphthalen-2-yl)-ethanone 14, was used to create a naphthyl derivative 8m for comparison to the acetophenone derived chalcones like 8b. As shown in Scheme 5 below, benzaldehyde derivative 6a was condensed with ketone 14 to give a 49% yield of the expected chalcone 8m. This reaction was sluggish and required extensive heating at 85° C. Surprisingly, efforts to synthesize the corresponding 3-hydroxy system 9m, using our standard method (35% $H_2O_2$/KOH) resulted in oxidative cleavage of the compound. Specifically, the related cinnamic acid derivative, 15 (74%) and only a trace of 9m were obtained.

In this instance, the 1-(1-hydroxy-naphthen-2-yl)prop-2-en-1-one system (e.g., 8m) behaved as a carboxylic acid precursor. Since this system is also highly fluorescent, it may have utility as a carboxylic acid protecting group. Furthermore, it is noted that the naphthyl system 8m was the only member of the chalcone series where this oxidative cleavage reaction occurred to a major extent. While not wishing to be bound by theory, this transformation likely occurred via a Baeyer-Villager rearrangement involving peroxide attack on the more electrophilic naphthyl ketone.

Scheme 5a

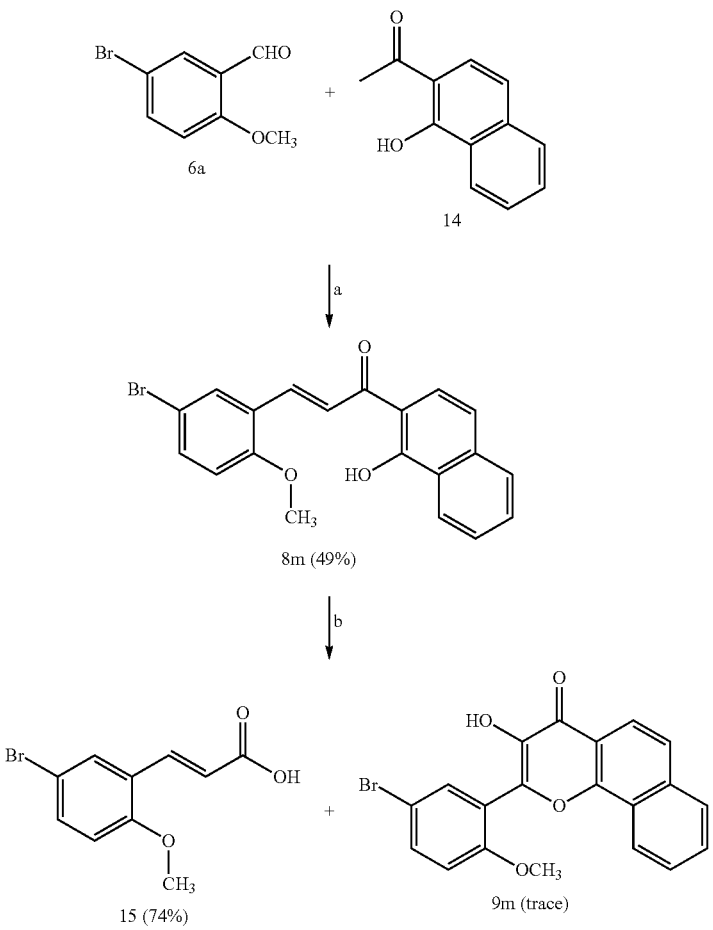

[a]Reagents: (a) 40% KOH/MeOH, $K_2CO_3$, 85° C.; (b) 35% $H_2O_2$, KOH/96% EtOH In another embodiment, disclosed are other useful compounds 16, 17, 18, and 19. These compounds may be used in accordance with the methods for treating and/or preventing a disease mediated by US28 receptor activity as taught herein. For example, these compounds may be used for treating or preventing viral infections, (e.g., Herpes simplex, HIV, HCMV).

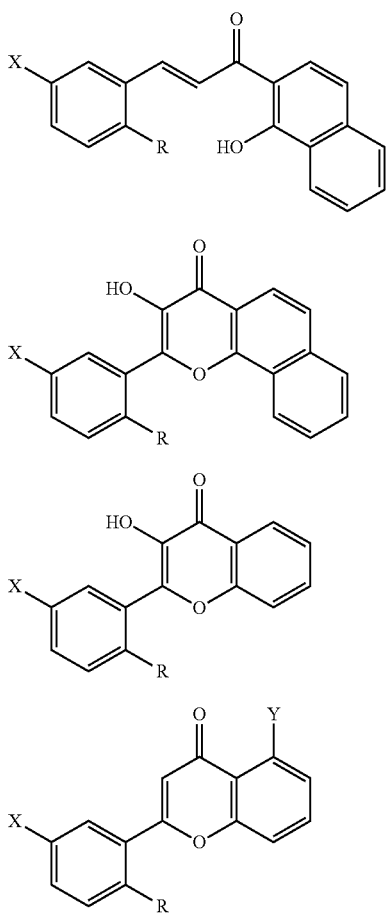

For compounds 16-19, R may be a hydrogen, hydroxy, halo, haloalkyl, thiocarbonyl, alkoxy, alkenoxy, alkylaryloxy, aryloxy, arylalkyloxy, cyano, nitro, imino, alkylamino, aminoalkyl, thio, sulfhydryl, thioalkyl, alkylthio, sulfonyl, $C_1$-$C_6$ straight or branched chain alkyl, $C_2$-$C_6$ straight or branched chain alkenyl or alkynyl, aryl, aralkyl, heteroaryl, carbocycle, or heterocycle group or moiety, or $CO_2R'$ where R' is hydrogen or $C_1$-$C_9$ straight or branched chain alkyl or $C_2$-$C_9$ straight or branched chain alkenyl group or moiety. In a specific embodiment, R is OEt, OMe, or OiPr. X may be a halogen, hydroxy or hydrogen. The halogen may include a chloro, bromo, fluoro, or iodo group. For compound 19, Y may be OBn or $OCH_2Ph$-(4-OMe) or $OCH_2Ph$-(4-OH).

1.3. BIOEVALUATION

Figures 2A, 2B:
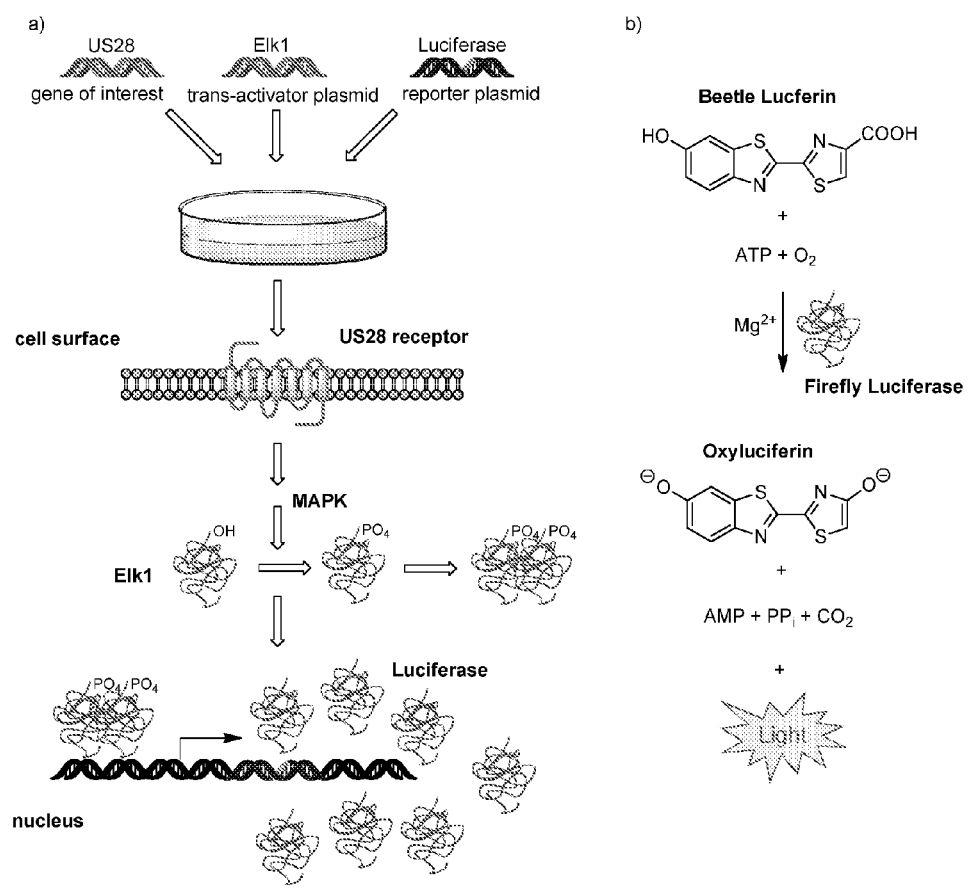
FIGS. 2A-2B depict the steps in (2A) a PathDetect Elk1 gene reporter assay and in (2B) a BrightGlo luminescence reaction.

Having generated a homologous series of chalcones and flavones, their ability to interact with the US28 receptor in human embryonic kidney (HEK) cells was investigated using an Elk-1 gene reporter assay (FIG. 2). HEK cells were transfected with either an empty vector (i.e., mock cells) or with a vector carrying US 28. These matched HEK cells provided a means to evaluate off-target effects as well as innate drug toxicity. As many of the flavonoid drugs were not water-soluble, all drug stock solutions were made in 100% dimethylsulfoxide (DMSO). The final DMSO concentration for each cell-based experiment, however, was 1% DMSO. To account for the presence of DMSO, 1% DMSO controls were run in parallel. 1050 values of the homologous series were also determined in Chinese hamster ovary (CHO) cells in order to assess the relative toxicities of each member of the series in a different cell line (see Table 1).

1.3.1 US28 Study

Interaction with the US28 receptor was measured by a decrease in luminescence using a firefly (*Photinus pyralis*) luciferase-based PathDetect Elk1 gene reporter assay (FIG. 2).[23,24] This assay assessed the modulation of US28-mediated activation of mitogen-activated protein kinase (MAPK) signaling pathways (results are shown in Table 1). In this regard, the compounds which have antagonist or inverse agonism on the upstream US28 receptor target can be considered MAPK inhibitors as reductions in upstream US28 signaling will result in downstream reductions in MAPK signaling. Such compounds which reduce MAPK signaling will have direct utility in the treatment of proliferative disorders including but not limited cancer.

As shown in FIG. 2, the pathway-specific fusion transactivator plasmid (containing GAL4 dbd and Elk1) and the gene of interest (US28) are cotransfected with the report plasmid containing GAL4 UAS and luciferase. After transfection the US28 is expressed and activates MAPK. The MAPK phosphorylates the activator domain of the GAL4dbd/Elk1 fusion protein, and causes its dimerization. The dimer then binds to the GAL4 UAS region of the reporter gene and allows for luciferase transcription. The luciferase mRNA is then translated and the luciferase protein is detected via luminescence by the use of the Bright-Glo reagent.

As a control, the empty pcDNA3 plasmid vector and the components of PathDetect system were also used for mock transfection of 293T HEK cells. Controls containing 1% DMSO were run in parallel. The relative luminescence results found with mock transfected 293T HEK cells treated with 10 μM drug and the untreated 1% DMSO control were compared via the following Equation 1.

% Effect on mock cells=(100%×(mock cell luminescence/DMSO control luminescence))−100%  Equation (1)

This equation was derived in order to assess the net effect each compound had on non-US28 containing HEK cells transfected via the same protocol. These control experiments were critical as they provided a method to address off target effects such as compound toxicity, which could give rise to false positives in the PathDetect assay.

Compounds, which had no off-target effects, gave nearly identical luminescence values in both the mock cells and the 1% DMSO control (i.e., a mock cell luminescence/DMSO control luminescence ratio of 1) and a net effect of 0% via Equation 1 (e.g., 9j: 0% in Table 1). In contrast, compounds that were stimulatory to the treated HEK cells gave higher mock cell luminescence than the DMSO control, a ratio >1, and a net positive value in Equation 1 for the % effect on mock cells (e.g., 8f: 290%). On the other hand, compounds that were intrinsically toxic gave lower luminescence in the treated mock cells than the DMSO control, a ratio below 1, and a net negative value for the % effect on mock cells (e.g., 8d: ~42%).

For discussion purposes, compounds that gave % effect values near zero (±15%), were considered as having little effect on HEK cells transfected with empty vector. Using this criterion most of the compounds tested had % effects on mock cells near zero. An ideal outcome was observed for 11b which had no effect on mock cells (−3% effect) and yet had dramatic negative efficacy values in the PathDetect assay (−89% efficacy). In this regard, 11b was confidently assigned as an inverse agonist of the US28 receptor.

The most significant exceptions were compounds 8f (290%), 8g (100%), 8i (33%), and 8m (35%), which at 10 µM had significantly positive % effect values on mock cells (via Equation 1), while at the same time being potent inverse agonists of the US28 receptor signaling pathway with ~95%, ~94%, ~76% and ~92% efficacies, respectively (see Table 1). Several compounds also provided the opposite effect. For example, as shown in Table 1, compounds 8b (~29%), 8d (~42%), 8h (~30%), 9c (~31%), 9d (~28%), and 11a (~40%) at 10 µM had significant negative % effect values on mock cells and had inverse agonist efficacies of ~44%, ~52%, ~58%, ~41%, ND, and ~49%, respectively. These latter compounds likely caused a decrease in mock cell luminescence versus the 1% DMSO control due to their toxicity.

According to the % efficacy observed in the Elk-1 assay, most of the compounds which contained a halogen within their structure gave inverse agonist activity ranging from −19% efficacy observed for 9a to ~95% for 8f. In contrast, the two non-halogen-containing compounds 8a and 8j displayed agonistic activity with efficacies of 67% and 52%, respectively. The $EC_{50}$ values ranged from 0.31 µM with 9i to >10 µM observed with 9b, 9d-9g, 11c, 12a, 12b, 13b, and 13h. Compounds 8k and 8l were found to be very toxic at 10 µM and were not tested further.

1.3.2 CHO Study

The $IC_{50}$ value of each compound was determined in CHO cells after a 48 hour incubation period at 37° C. using the MTS assay to assess compound toxicity in a separate cell line.[25] This information allowed for the ranking of systems via their toxicity profiles in the CHO line. The 48 hour CHO IC50 values are shown in Table 1. In each case, the chalcone system 8 was more toxic than the corresponding ring-closed system, 9.

1.3.3 Results

TABLE 1 a Bioevaluation of 8-9 and 11-13 in transfected human embryonic kidney (HEK) 293T cells containing the US28 receptor (columns 2-4), non-transfected HEK cells (column 5) and their $IC_{50}$ values (µM) in CHO cells (column 6).

| Compound | $EC_{50}$ (µM)[b] | $pEC_{50}$ ± SEM[b] | Efficacy(%) | Effect(%) on mock cells with each drug at 10 µM[c] | CHO 48 h $IC_{50}$ value (µM)[d] |
|---|---|---|---|---|---|
| 8a | 1.4 | 5.84 ± 0.29 | 67% | 8% | 25.5 ± 2.7 |
| 8b | 7.8 | 5.11 ± 0.03 | ~44% | −29% | 8.7 ± 0.3 |
| 8c | 5.0 | 5.30 ± 0.03 | ~88% | −3% | 7.2 ± 0.5 |
| 8d | 6.7 | 5.18 ± 0.10 | ~52% | −42% | 7.2 ± 0.4 |
| 8e | 4.9 | 5.31 ± 0.07 | ~55% | 5% | 16.9 ± 1.3 |
| 8f | 6.0 | 5.22 ± 0.06 | ~95% | 290% | 6.1 ± 0.8 |
| 8g | 5.5 | 5.26 ± 0.05 | ~94% | 100% | 6.7 ± 0.7 |
| 8h | 7.8 | 5.11 ± 0.03 | ~58% | −30% | 8.4 ± 0.6 |
| 8i | 6.4 | 5.19 ± 0.02 | ~76% | 33% | 6.8 ± 0.9 |
| 8j | 10 (single concentration) | ND | +52% | −4% | 14.2 ± 2.7 |
| 8k | Toxic | — | — | Toxic | ND |
| 8l | Toxic | — | — | Toxic | 8.1 ± 1.0 |
| 8m | 2.9 | 5.54 ± 0.04 | −92% | 35% | 15.6 ± 1.0 |
| 9a | 4.6 | 5.34 ± 0.19 | −19% | −1% | >100 |
| 9b | NE | — | — | −11% | 88.5 ± 10.1 |
| 9c | 0.8 | 6.08 ± 0.17 | −41% | −31% | 13.5 ± 1.3 |
| 9d | NE | — | — | −28% | >100 |
| 9e | NE | — | — | −17% | 18.3 ± 2.5 |
| 9f | NE | — | — | −1% | 17.3 ± 1.9 |
| 9g | NE | — | — | −23% | 17.9 ± 1.6 |
| 9h | 1.32 | 5.88 ± 0.22 | −42% | 2% | 25.0 ± 2.2 |
| 9i | 0.31 | 6.51 ± 0.14 | −41% | −17% | >100 |
| 9j | 1.78 | 5.75 ± 0.25 | −38% | 0% | 54.6 ± 4.2 |
| 11a | 7.3 | 5.14 ± 0.10 | −49% | −40% | 17.5 ± 1.9 |
| 11b | 3.5 | 5.46 ± 0.09 | −89% | −3% | 96.6 ± 5.6 |
| 11c | NE | — | — | 3% | 64.8 ± 8.1 |
| 11d | 8.1 | 5.09 ± 0.10 | −55% | −17% | >100 |
| 12a | NE | — | — | 2% | >100 |
| 12b | NE | — | — | −16% | 75.2 ± 8.7 |

TABLE 1-continued a Bioevaluation of 8-9 and 11-13 in transfected human embryonic kidney
(HEK) 293T cells containing the US28 receptor (columns 2-4), non-transfected HEK cells
(column 5) and their $IC_{50}$ values (μM) in CHO cells (column 6).

| Compound | $EC_{50}$ (μM)[b] | $pEC_{50}$ ± SEM[b] | Efficacy(%) | Effect(%) on mock cells with each drug at 10 μM[c] | CHO 48 h $IC_{50}$ value (μM)[d] |
|---|---|---|---|---|---|
| 13b | NE | — | — | −5% | 67.9 ± 9.3 |
| 13h | NE | — | — | −14% | | a Functional data were obtained on 293T HEK cells that transiently expressed US28 and components of the PathDetect trans Elk1 reporter gene system.[24] Dose response curves of 3-5 experiments (performed in triplicates) were normalized and pooled to get a mean curve from which the $EC_{50}$ value and the maximum intrinsic activity of each compound was obtained. A dash line indicates that the analysis was not performed due to the $EC_{50}$ being greater than 10 μM. The resulting reporter gene assay data were analyzed by nonlinear regression using the algorithms in PRISM 5.0 (GraphPad Software, San Diego, CA).
[b]Curves were fitted to the sigmoid curve by non-linear regression analysis in which the logEC50 values (pEC50 ± SEM) were determined.
NE = no effect when tested at 10 μM of compound;
ND = not determined;
[c]The effect (%) on mock cells was determined for selected compounds at a fixed 10 μM concentration vs an untreated control group containing 1% DMSO in order to rank the relative non-specific effects of the compounds in the mock transfected HEK cell line. The substances that exerted a change in luminescence greater than ±10% of the DMSO control were identified as substances which exert non-specific effects on the cells, which were not related to US28 signaling. These non-specific, off-target effects may include compound toxicity.
[d]CHO cells were incubated for 48 h at 37° C. with the respective compound and relative cell viability assessed with the MTS reagent.[25a]

As shown in Table 1, seventeen of the thirty one compounds showed some activity against the US28 receptor target. There were several structural classes evaluated, namely chalcones 8, flavonols 9, 4H-chromen-4-ones (11 and 12) and chroman-4-ones 13.

In general, chalcones 8 were better inverse agonists than their corresponding cyclic flavonoids, with the exception of 4H-chromen-4-one 11b. However, several chalcones also influenced the luminescence of mock-transfected cells. The exceptions were chalcones 8a, 8c, 8e, and 8j which showed % effect values near zero in Table 1. An interesting observation was that all the halogen substituted chalcones (8b-i, 8m) were characterized as inverse agonists, whereas the hydro derivative (8a) and methyl derivative (8j) showed agonist activity on the US28 receptor. We speculate that this observation may be due to the novel ability of halogen-substituted drugs to interact with their protein targets.[25b] Toxicity was observed for many of the chalcones when tested in the 10 μM concentration range with HEK cells and while incubating them with CHO cells for 48 hours. Indeed, cytotoxicity, which is well described for other chalcone scaffolds,[1a] might be the reason for the off-target (non-US28) effects observed with several of the chalcones on the mock-transfected cells.

Interestingly, the hydro- and methyl-substituted cyclic flavonols (9a and 9j) in contrast to their chalcone analogs (8a and 8j) inhibited US28 receptor constitutive activity. We noted that the chloro-substituted derivative 9h was an inverse agonist of US28 (~42% efficacy) and had little effect on mock cells (2% effect), whereas the bromo-substituted derivative 9b did not show any activity on the US28 receptor at 10 μM. Flavonols 9c and 9i, bearing the ethoxy-instead of the methoxy-substituent on their skeleton, inhibited US28 activity as well, but at the same time showed some non-US28 related effects on mock-transfected cells (~31 and ~17% effect, respectively). While chroman-4-ones 13b and 13h did not have any significant effect on US28 receptor, compound 11b, which contained a 4-H-chromen-4-one structure was one of the most efficacious US28 receptor inverse agonists of the series tested (with −89% efficacy). Compound 11b had essentially no effect on mock-transfected cells (% effect=~3%) and was essentially non-toxic to CHO cells (CHO $IC_{50}$=96.6 μM). Its analogues without the bromo- or benzoxy-substituent (11a and 11d respectively) showed lower efficacy (~49% and −55%) and increased non-specific effects on mock cells (~40% and ~17%). The removal of both the bromo- and benzoxy-substituents (analog 11c) resulted in an inactive ligand.

Compound 11b is a significant discovery because it is a full inverse agonist of US28 receptor signaling (with an $EC_{50}$ value of 3.5 μM and efficacy of −89%, Table 1) and was not toxic. In this regard, compound 11b represents the preferred balance of high potency, strong negative efficacy and low toxicity. While several other flavonoid derivatives (9) in Table 1 were more potent (e.g., 9c and 9h-9j have lower $EC_{50}$ values in Table 1), none of these were as efficacious (11b: ~89% efficacy).

The findings are especially important because only two other drug classes have been reported to inhibit US28 constitutive activity. The non-peptidergic CCR 1 antagonist,[26] VUF2274 5a, and its derivatives have been characterized as inverse agonists for US28 in the PLCβ signaling pathway (as measured by an accumulation of inositol triphosphate).[27,28] Compound 5a has also been evaluated via the same Elk1 reporter assay used in Table 1 and gave an $EC_{50}$ value of 4.5 μM and efficacy of ~22%.[13] In addition, dihydroisoquinolinones 5b and tetrahydroisoquinolines 5c have also been identified as promising lead scaffolds for inhibition of US28 constitutive activity in the p42/p44 mitogen-activated protein kinase (MAPK) and p38 MAPK-dependent pathways.[13] In this regard, compound 11b identifies new chemical space with this property and provides an architecture which can be accessed on large scale in a limited number of synthetic steps.

1.3.4 Biological Investigations

The efficacy of each compound on the US28 receptor was investigated in luciferase based reporter gene assay Path-Detect trans Elk1 (Agilent, Stratagene)[23] as described previously.[13] Briefly, the human embryonic kidney (HEK) 293T cells were transiently-transfected with 0.1 μg Elk1, 5 μg Luc, and 5 μg of US28 vector or empty pcDNA3 vector (mock cells). Five hours after transfection, the cells were washed with DMEM containing 1% FBS, harvested, seeded in a white half-area 96-well plate (20,000 cells/well) and incubated with the indicated concentrations of test compounds. The incubation buffer consisted of DMEM, 1% FBS, 2 mM L-glutamine, 1% penicillin-streptomycin and 1% DMSO. The cells were incubated at 37° C. in the humid atmosphere with 5% $CO_2$ for an additional 20-24 hours. The luciferase substrate BrightGlo (Promega) was used according to the manufacturer's instruction. The luminescence intensity was acquired using microplate reader Victor3V (Perkin-Elmer). The basal luminescence of mock transfected cells was approximately 500 RLU and the basal luminescence of US28-transfected cells was 4-5-fold higher (2000-2500 RLU). As the inhibitors gave differential responses in terms of their ability to reduce US 28 mediated signaling, their relative $EC_{50}$ values were determined by dosing the US-28 transfected HEK cells with increasing concentrations of each compound. In this case, the $EC_{50}$ value is the concentration of the compound needed to provoke a response halfway between the compound's maximal response (change in luminescence) and the no-compound control in the same US-28 transfected cell line. A plot of relative luminescence versus log of the compound concentration provided a dose-response curve from which the % efficacy was derived via non-linear regression methods using the algorithms in PRISM 5.0 (GraphPad Software, San Diego, Calif.). The data is tabulated in Table 1.

The CHO assay was conducted to assess the general toxicity of each flavonoid drug. Briefly, cell growth was assayed in sterile 96-well microtiter plates (Costar 3599, Corning, N.Y., USA) in the presence of each drug. Experiments were conducted in triplicate. CHO cells were plated at 10,000 cells/mL. Drug solutions were prepared in 100% DMSO and dosed so that the final DMSO concentration was <1%. For example, 1 µL of drug solution was added to the CHO cells plated in each well in 100 µL of media. Drug additions occurred after an initial overnight incubation of CHO cells in each well. After drug was added, the cells were incubated in 5% CO2 for 48 h at 37° C. The MTS reagent (Promega Cell Titer 96 Aqueous non-radioactive cell proliferation reagent) was added (20 µL) and the CHO cells were incubated for an additional 4h and then absorbance at 490 nm was measured on a BioTek Synergy MX plate reader. Controls run using 1% DMSO in the media and no drug showed toxicity over the 48 h period compared to CHO cells grown in media only. $IC_{50}$ values were determined from the corresponding plot of relative absorbance at 490 nm vs drug concentration. The data is tabulated in Table 1.

Figure 3:
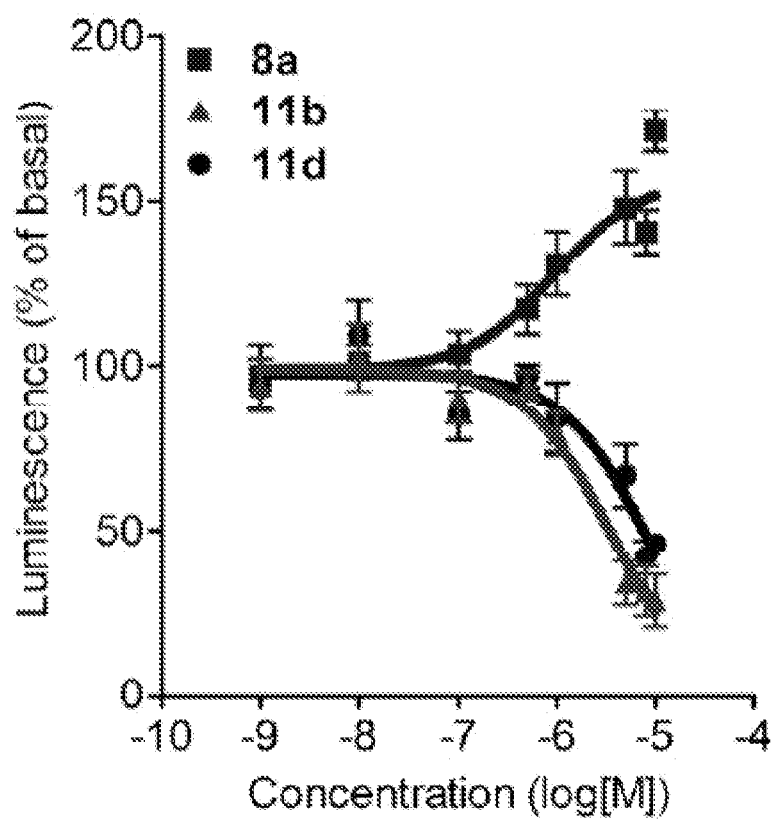
FIG. 3 shows the bioevaluation of representative novel compounds with agonist 8a, and inverse agonists 11b and 11d.
Figure 4A:
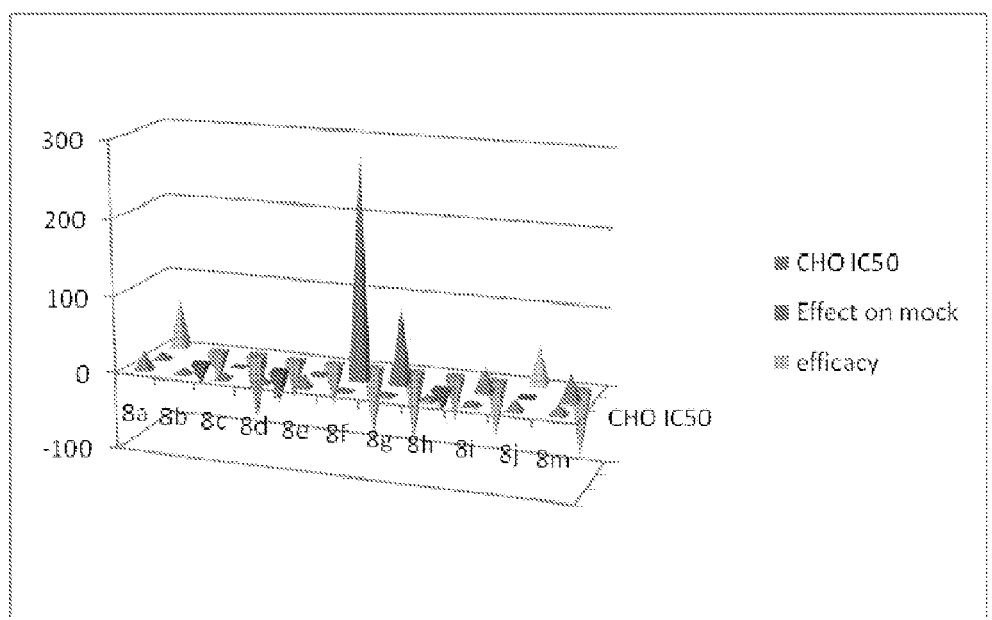
FIGS. 4A-4B are 3D plots showing the relative performance of selected members from each structure class 8 and 9, in terms of efficacy, % effect on mock cells and CHO toxicity.
Figure 4B:
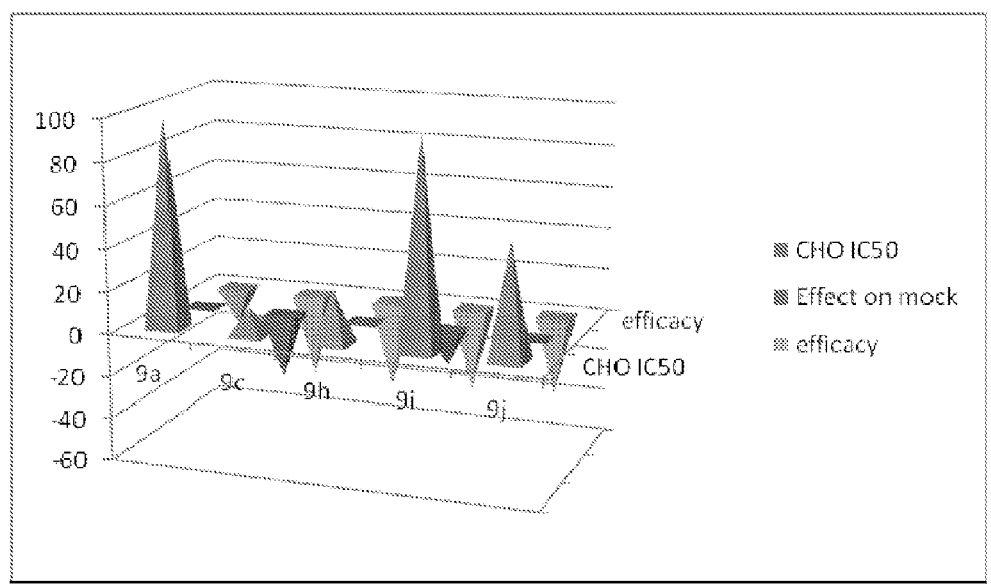
Figure 5:
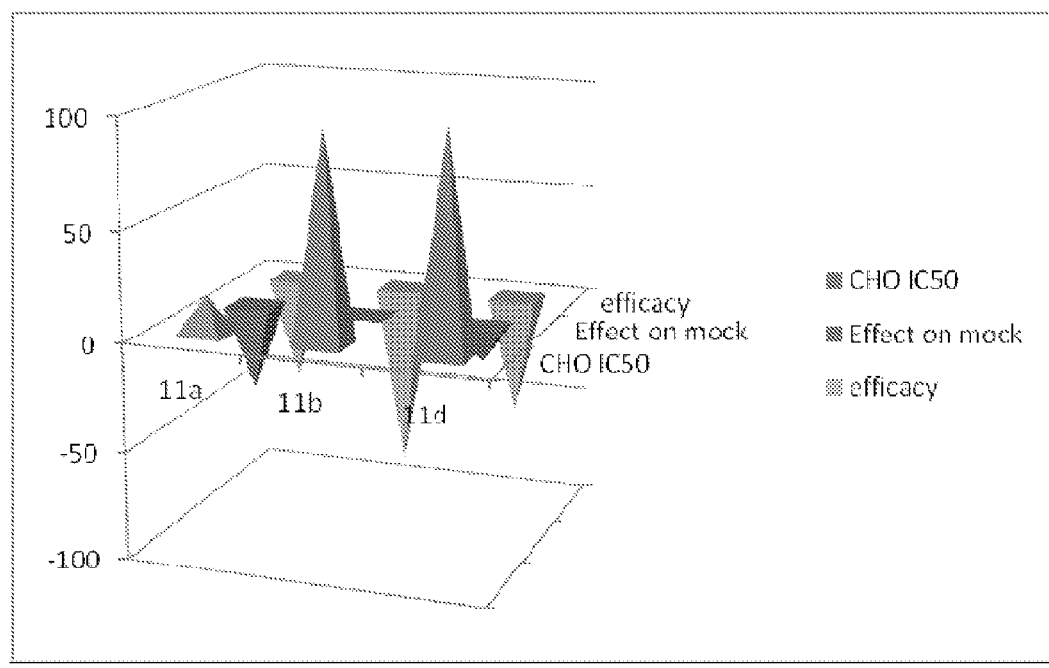
FIG. 5 is a 3D plot showing the relative performance of selected members of the 11 series in terms of efficacy, % effect on mock cells and CHO toxicity. Compound 11b, for example, had the desirable properties of high CHO IC50 value (an indication of low toxicity), near zero effect on mock cells (showing specificity for the US28 target) and a strong inverse agonism activity.

FIG. 3 shows the bioevaluation of representative novel compounds 8a, 11b and 11d. 293T HEK cells were transiently-transfected with US28 and components of PathDetect Elk1 reporter gene assay. Dose-response curves shown resulted from pooled data from 3-5 experiments, each performed in triplicate. The error bars represent the SEM. FIG. 3 demonstrates the agonism of 8a and the inverse agonism of 11b and 11d.

1.3.5. HIV Assays

Assays were performed below in accordance with the procedures set forth in The Journal of Immunology, 2006, 176, pp. 6900-905; AIDS Research and Human Retroviruses, 2004, 20:11, pp. 1157-1665.[32,33]

a) Effect on Cell Viability and Growth (Experiment 1A)

TZMbI assays for cell safety were performed to identify potential anti-viral compounds. The results are shown below in Table 2.

TABLE 2

(Effect on Cell Viability and Growth using CytoTox Glo assay, Promega, Madison, WI)

| Treatment | Dose | (% decrease in viability compared to 0.1% DMSO vehicle based on viable cell luminescence) |
|---|---|---|
| Media change only | 0.0% additives | |
| 1% DMSO | 1% DMSO | |
| 0.1% DMSO | 10 µM equivalent | |
| 8a | 10 µM | 18.7 |
| 8b | 10 µM | 64.2 |
| 8c | 10 µM | 53.3 |
| 1d | 10 µM | 72.9 |
| 8e | 10 µM | 4.1 |
| 8f | 10 µM | 91.3 |
| 8g | 10 µM | 99.7 |
| 8h | 10 µM | 98.9 |
| 8i | 10 µM | 87.1 |
| Media change only | 0.0% additives | |
| 1% DMSO | 1% DMSO | |
| 0.1% DMSO | 10 µM equivalent | |
| 8j | 10 µM | 47.0 |
| 8l | 10 µM | 29.8 |
| 8m | 10 µM | 20.3 |
| 9b | 10 µM | -2.1 |
| 9c | 10 µM | -8.9 |
| 9d | 10 µM | -7.3 |
| 9e | 10 µM | -11.9 |
| 9f | 10 µM | -0.2 |
| Media change only | 0.0% additives | |
| 1% D MSO | 1% DMSO | |
| 0.1% DMSO | 10 µM equivalent | |
| 9g | 10 µM | 15.3 |
| 9h | 10 µM | 23.6 |
| 9i | 10 µM | 21.8 |
| 9j | 10 µM | 4.8 |
| 11b | 10 µM | 6.4 |
| 11c | 10 µM | 39.5 |
| 11d | 10 µM | 23.6 |
| 12a | 10 µM | 44.5 |
| 12b | 10 µM | 34.9 |
| Media change only | 0.0% additives | |
| 1% DMSO | 1% DMSO | |
| 0.1% DMSO | 10 µM equivalent | |
| 13b | 10 µM | -9.1 | b) Anti-HIV Assay (Experiment 1B)

Cells were treated with 2 ng/mL p24 of HIV-1 BaL administered; MOI approx 0.02 (see refs 32, 33). The results are shown below in Table 3.

TABLE 3

(HIV Inhibition)

| Treatment | Dose | RLU (RLU, relative luciferase units) | Mean % Inhibition of Infection |
|---|---|---|---|
| Media change only | 0.0% additives | 2.3 | |
| 1% DMSO | 1% DMSO | 1733.4 | |
| 0.1% DMSO | 10 µM equivalent | 945.9 | |
| 8a | 10 µM | 1218.5 | -28.8 |
| 8b | 10 µM | 202.3 | 78.6 |
| 8c | 10 µM | 112.3 | 88.1 |
| 8d | 10 µM | 134.6 | 85.8 |
| 8e | 10 µM | 671.4 | 29.0 |
| 8f | 10 µM | 45.9 | 95.1 |
| 8g | 10 µM | 3.3 | 99.6 |
| 8h | 10 µM | 33.8 | 96.4 |
| 8i | 10 µM | 130.4 | 86.2 |
| Media change only | 0.0% additives | 2.2 | |
| 1% DMSO | 1% DMSO | 1633.0 | |
| 0.1% DMSO | 10 µM equivalent | 936.7 | |

TABLE 3-continued (HIV Inhibition)

| Treatment | Dose | RLU (RLU, relative luciferase units) | Mean % Inhibition of Infection |
|---|---|---|---|
| 8j | 10 μM | 345.7 | 63.1 |
| 8l | 10 μM | 57.3 | 93.9 |
| 8m | 10 μM | 437.6 | 53.3 |
| 9b | 10 μM | 736.7 | 21.3 |
| 9c | 10 μM | 727.6 | 22.3 |
| 9d | 10 μM | 452.5 | 51.7 |
| 9e | 10 μM | 693.9 | 25.9 |
| 9f | 10 μM | 528.5 | 43.6 |
| Media change only | 0.0% additives | 2.4 | |
| 1% DMSO | 1% DMSO | 1756.7 | |
| 0.1% DMSO | 10 μM equivalent | 936.0 | |
| 9g | 10 μM | 358.6 | 61.7 |
| 9h | 10 μM | 367.6 | 60.7 |
| 9i | 10 μM | 361.0 | 61.4 |
| 9j | 10 μM | 814.0 | 13.0 |
| 11b | 10 μM | 781.6 | 16.5 |
| 11c | 10 μM | 235.6 | 74.8 |
| 11d | 10 μM | 576.3 | 38.4 |
| 12a | 10 μM | 152.1 | 83.7 |
| 12b | 10 μM | 445.1 | 52.4 |
| Media change only | 0.0% additives | 2.1 | |
| 1% DMSO | 1% DMSO | 1637.3 | |
| 0.1% DMSO | 10 μM equivalent | 910.0 | |
| 13b | 10 μM | 884.5 | 2.8 | c) Dose Response Curves (Effect on Cell Viability and Growth (Experiment 2A)

TZMbI assays for cell safety were performed to identify potential anti-viral compounds per the methods. The results are shown below in Table 4.

TABLE 4

(Dose Response-Effect on Cell Viability and Growth)

| Treatment | Dose | (% decrease in viability compared to 0.1% DMSO vehicle based on viable cell luminescence) |
|---|---|---|
| Media change only | | |
| RC-101 vehicle (0.01% acetic acid) | 10 μM | |
| RC-101 | 10 μM equivalent | −1.43 |
| DMSO | 20 μM | |
| DMSO | 10 μM | |
| DMSO | 5 μM | |
| DMSO | 2.5 μM | |
| DMSO | 1.25 μM | |
| 8l | 20 μM | 55.17 |
| 8l | 10 μM | 28.73 |
| 8l | 5 μM | 2.20 |
| 8l | 2.5 μM | −0.43 |
| 8l | 1.25 μM | −2.83 |
| 8m | 20 μM | 90.01 |
| 8m | 10 μM | 38.18 |
| 8m | 5 μM | 10.68 |
| 8m | 2.5 μM | 17.85 |
| 8m | 1.25 μM | 10.35 |
| 9i | 20 μM | 21.57 |
| 9i | 10 μM | 18.69 |
| 9i | 5 μM | 10.66 |
| 9i | 2.5 μM | 6.19 |
| 9i | 1.25 μM | 10.75 |
| 9c | 40 μM | 64.18 |
| 9c | 20 μM | 14.81 |
| 9c | 10 μM | 0.10 |
| 9c | 5 μM | −0.19 |
| 9c | 2.5 μM | −6.23 |
| 9h | 20 μM | 7.83 |
| 9h | 10 μM | 1.57 |
| 9h | 5 μM | −13.94 |
| 9h | 2.5 μM | −10.36 |
| 9h | 1.25 μM | −8.02 |
| 12a | 20 μM | 130.53 |
| 12a | 10 μM | 43.05 |
| 12a | 5 μM | 123.40 |
| 12a | 2.5 μM | 41.73 |
| 12a | 1.25 μM | 6.38 |
| 12b | 20 μM | 49.14 |
| 12b | 10 μM | 10.36 |
| 12b | 5 μM | −3.20 |
| 12b | 2.5 μM | −2.40 |
| 12b | 1.25 μM | −8.84 |
| 11b | 80 μM | −1.51 |
| 11b | 40 μM | −29.19 |
| 11b | 20 μM | −18.09 |
| 11b | 10 μM | −5.05 |
| 11b | 5 μM | −6.17 |
| 9a | 80 μM | −7.86 |
| 9a | 40 μM | −25.38 |
| 9a | 20 μM | −21.57 |
| 9a | 10 μM | −24.90 |
| 9a | 5 μM | −3.31 |
| 9b | 80 μM | 13.34 |
| 9b | 40 μM | −29.81 |
| 9b | 20 μM | −25.87 |
| 9b | 10 μM | −19.04 |
| 9b | 5 μM | −7.08 |
| 9d | 80 μM | −8.38 |
| 9d | 40 μM | −33.15 |
| 9d | 20 μM | −23.71 |
| 9d | 10 μM | −18.61 |
| 9d | 5 μM | −7.87 | b) Anti-HIV Assay (Experiment 2B)

Cells were treated with 2 ng/mL p24 of HIV-1 BaL administered; MOI approx 0.02 (see refs 32, 33). The results are shown below in Table 5.

TABLE 5

(Dose Response-HIV Inhibition)

| Treatment | Dose | RLU (RLU, relative luciferase units) | Mean % Inhibition of Infection |
|---|---|---|---|
| Media change only | 0.0% additives | 1.17 | |
| Media change only | 1% DMSO | 254.22 | |
| RC-101 (0.1% acetic acid) | 10 μM | 267.9 | |
| RC-101 | 10 μM | 1.67 | 99.38 |
| DMSO | 20 μM | 319.8 | |
| DMSO | 10 μM | 273.4 | |
| DMSO | 5 μM | 276.0 | |
| DMSO | 2.5 μM | 259.9 | |
| DMSO | 1.25 μM | 260.8 | |
| 8l | 20 μM | 16.87 | 94.73 |
| 8l | 10 μM | 23.18 | 91.52 |
| 8l | 5 μM | 125.95 | 54.36 |
| 8l | 2.5 μM | 215.14 | 17.21 |
| 8l | 1.25 μM | 262.26 | −0.55 |
| 8m | 20 μM | 160.21 | 49.91 |
| 8m | 10 μM | 170.42 | 37.66 |
| 8m | 5 μM | 251.02 | 9.04 |
| 8m | 2.5 μM | 283.48 | −9.08 |

TABLE 5-continued (Dose Response-HIV Inhibition)

| Treatment | Dose | RLU (RLU, relative luciferase units) | Mean % Inhibition of Infection |
|---|---|---|---|
| 8m | 1.25 μM | 324.10 | −24.26 |
| 9i | 20 μM | 81.12 | 74.64 |
| 9i | 10 μM | 159.94 | 41.49 |
| 9i | 5 μM | 204.06 | 26.06 |
| 9i | 2.5 μM | 238.44 | 8.25 |
| 9i | 1.25 μM | 254.23 | 2.53 |
| 9c | 40 μM | 88.45 | 64.18 |
| 9c | 20 μM | 69.09 | 14.81 |
| 9c | 10 μM | 49.29 | 0.10 |
| 9c | 5 μM | 33.63 | −0.19 |
| 9c | 2.5 μM | 30.81 | −6.23 |
| 9h | 20 μM | 20.14 | 7.83 |
| 9h | 10 μM | 49.04 | 1.57 |
| 9h | 5 μM | 18.32 | −13.94 |
| 9h | 2.5 μM | 16.44 | −10.36 |
| 9h | 1.25 μM | 1.61 | −8.02 |
| 12a | 20 μM | 88.46 | 130.53 |
| 12a | 10 μM | 83.62 | 43.05 |
| 12a | 5 μM | 56.78 | 123.40 |
| 12a | 2.5 μM | 28.09 | 41.73 |
| 12a | 1.25 μM | −3.22 | 6.38 |
| 12b | 20 μM | 36.35 | 49.14 |
| 12b | 10 μM | 27.57 | 10.36 |
| 12b | 5 μM | −1.73 | −3.20 |
| 12b | 2.5 μM | 0.82 | −2.40 |
| 12b | 1.25 μM | −7.32 | −8.84 |
| 11b | 80 μM | 62.68 | −1.51 |
| 11b | 40 μM | 49.22 | −29.19 |
| 11b | 20 μM | 40.47 | −18.09 |
| 11b | 10 μM | 34.09 | −15.05 |
| 11b | 5 μM | 24.27 | −6.17 |
| 9a | 80 μM | 59.24 | −7.86 |
| 9a | 40 μM | 65.50 | −25.38 |
| 9a | 20 μM | 36.83 | −21.87 |
| 9a | 10 μM | 16.51 | −24.90 |
| 9a | 5 μM | 16.52 | −3.31 |
| 9b | 80 μM | 73.47 | 13.34 |
| 9b | 40 μM | 47.61 | −29.81 |
| 9b | 20 μM | 32.82 | −25.87 |
| 9b | 10 μM | 23.85 | −19.04 |
| 9b | 5 μM | 12.99 | −7.08 |
| 9d | 80 μM | 59.85 | −8.38 |
| 9d | 40 μM | 68.82 | −33.15 |
| 9d | 20 μM | 41.25 | −23.71 |
| 9d | 10 μM | 25.14 | −18.61 |
| 9d | 5 μM | 10.04 | −7.87 |

Compounds that gave the highest % inhibition at a low concentration were preferred. For example, compound 8l gave 54.36% inhibition at a 5 μM concentration, i.e. an $IC_{50} < 5$ μM, and was preferred.

1.4 PHARMACEUTICAL COMPOSITIONS

Aspects of the present invention also provide pharmaceutical compositions comprising one or more of the compounds described. The pharmaceutical compositions can be administered to a patient to achieve a desired therapeutic effect, e.g., inhibition of US28 constitutive activity. The compositions can be administered alone or in combination with at least one other agent, such as a stabilizing compound, which can be administered in any sterile, biocompatible pharmaceutical carrier, including, but not limited to, saline, buffered saline, dextrose, and water. The compositions can be administered to a subject alone, or in combination with other therapeutic agents or treatments as described below.

In addition to the active ingredients, these pharmaceutical compositions can contain suitable pharmaceutically acceptable carriers comprising excipients and auxiliaries that facilitate processing of the active compounds into preparations which can be used pharmaceutically. Pharmaceutical compositions of the invention can be administered by any number of routes including, but not limited to, oral, intravenous, intramuscular, intra-arterial, intramedullary, intrathecal, intraventricular, transdermal, subcutaneous, intraperitoneal, intranasal, parenteral, topical, sublingual, or rectal means. Pharmaceutical compositions for oral administration can be formulated using pharmaceutically acceptable carriers well known in the art in dosages suitable for oral administration. Such carriers enable the pharmaceutical compositions to be formulated as tablets, pills, dragees, capsules, liquids, gels, syrups, slurries, suspensions, and the like, for ingestion by the subject. In certain embodiments, the compositions are formulated for topical administration, such as in the form of a cream or gel. The cream or gel can be formulated as an aqueous fluid containing a soluble polymer as the thickening agent, for example. Alternately, the cream or gel may comprise a suspension or a colloidal solution, which contains insoluble particles suspended in a liquid carrier medium. See U.S. Pat. No. 5,208,031, the entirety of which is hereby incorporated by reference.

Further details on techniques for formulation and administration can be found in the latest edition of REMINGTON'S PHARMACEUTICAL SCIENCES (Mack Publishing Co., Easton, Pa., which is incorporated herein by reference). After pharmaceutical compositions have been prepared, they can be placed in an appropriate container and labeled for treatment of an indicated condition. Such labeling would include amount, frequency, and method of administration.

1.5 DETERMINATION OF A THERAPEUTICALLY EFFECTIVE DOSE

The determination of a therapeutically effective dose for any one or more of the compounds described herein is within the capability of those skilled in the art. A therapeutically effective dose refers to that amount of active ingredient which provides the desired result. The exact dosage will be determined by the practitioner, in light of factors related to the subject that requires treatment. Dosage and administration are adjusted to provide sufficient levels of the active ingredient or to maintain the desired effect. Factors which can be taken into account include the severity of the disorder state, general health of the subject, age, weight, and gender of the subject, diet, time and frequency of administration, drug combination(s), reaction sensitivities, and tolerance/response to therapy. Long-acting pharmaceutical compositions can be administered every 3 to 4 days, every week, or once every two weeks depending on the half-life and clearance rate of the particular formulation.

Normal dosage amounts can vary from 0.1 to 100,000 micrograms, up to a total dose of about 1 g, depending upon the route of administration. Guidance as to particular dosages and methods of delivery is provided in the literature and generally available to practitioners in the art. Preferably, a therapeutic agent gains access to the parasite or the infected red blood cell for the duration of time necessary for its normal action.

1.6 APPLICATIONS

The compounds and compositions as described herein may be utilized for the treatment or prevention of any disorder related to, modulated by, mediated by and/or associated with US28 receptor activity. Typically, the disorder involves a degree of undesired US28 receptor activity, which increases the likelihood of the disorder developing or the severity thereof. In one aspect, the compounds described herein may be used for treating or preventing proliferation of a virus. In an embodiment, the virus is a CMV infection or disorder associated with, or resultant from, CMV infection. In another aspect, the compounds described herein may be used for treating or preventing other virus infections, such as HIV-1 or HIV-2. It is appreciated that the compositions described herein may be particularly useful for the prevention or treatment of virus entry or viral proliferation, particularly in immuno-compromised individuals, such as in the case of transplants or other operations involving a patient diagnosed with HIV.

In yet another aspect, the compounds described herein may be utilized for treating or preventing cardiovascular disease or a disease or condition characterized by or involving acute inflammation or chronic inflammation. In still another aspect, the compounds described herein may be utilized for treating or preventing a proliferative disorder such as cancer, particularly those cancers involving possible or actual tumorigenesis. In one embodiment, the compositions described herein are utilized to prevent or treat HMCV-associated tumor progression. In still another aspect, the compositions described herein may be utilized to prevent or treat the proliferation of bacterial infections.

It is contemplated that the compositions described herein may be administered to a subject once a subject exhibits one or more symptoms of the above diseases as would be appreciated by one skilled in the art. In HCMV, for example, subjects infected with HCMV may initially show no symptoms. Once the infection flourishes, however, typical symptoms that may manifest include glandular fever, mild hepatitis, and sore throat. The infection may also occur if the immune system is suppressed either by drugs, other infection or old age.

1.7 CONJUNCTIVE THERAPEUTIC AGENTS

In any of the embodiments described above, any of the compounds and/or compositions of the invention can be co-administered with other appropriate therapeutic agents (conjunctive agent or conjunctive therapeutic agent) or therapies for the treatment or prevention of a disorder related to US28 receptor activity, e.g., signaling, and/or symptom(s) thereof. Such diseases may include conditions involving inflammation, cardiovascular disease, cancer, virus infection, such CMV or HCMV infection. Selection of the appropriate conjunctive agents or therapies for use in combination therapy can be made by one of ordinary skill in the art, according to conventional pharmaceutical principles. The combination of therapeutic agents or therapies can act synergistically to effect the treatment or prevention of the diseases or a symptom thereof. Using this approach, one may be able to achieve therapeutic efficacy with lower dosages of each agent, thus reducing the potential for adverse side effects.

In certain embodiments, the conjunctive agents may be an anti-viral agent as is known in the art. Exemplary antiviral agents include ganciclovir, foscarnet and cidofovir. Exemplary anti-HIV agents include indinavir, ritonavir, AZT, lamivudine and saquinavir. Exemplary immunosuppressive agents include cyclosporin and FK-506. The compositions may also be advantageously used as antiviral prophylactic treatment in combination with immunosuppressive protocols. In other embodiments, the conjunctive agent may be an anti-cancer therapy as is known in the art. In another embodiment, the ability of the compounds described herein (also described as US28 receptor modulators) to reduce MAPK signaling could be used in combination with other anti-proliferative drugs to reduce cell proliferation in cancer cells. Exemplary agents include difluoromethylornithine (DFMO) or Paclitaxel.

The mode of administration for a conjunctive formulation in accordance with the present invention is not particularly limited, provided that the compounds of the present invention as described herein ("novel US28 receptor modulator") and the conjunctive agent are combined upon administration. Such an administration mode may, for example, be (1) an administration of a single formulation obtained by formulating a novel US28 receptor modulator and a conjunctive agent simultaneously; (2) a simultaneous administration via an identical route of the two agents obtained by formulating a novel US28 receptor modulator and a conjunctive agent separately; (3) a sequential and intermittent administration via an identical route of the two agents obtained by formulating a novel US28 receptor modulator and a conjunctive agent separately; (4) a simultaneous administration via different routes of two formulations obtained by formulating a novel US28 receptor modulator and a conjunctive agent separately; and/or (5) a sequential and intermittent administration via different routes of two formulations obtained by formulating a novel US28 receptor modulator and a conjunctive agent separately (for example, a novel US28 receptor modulator followed by a conjunctive agent, or inverse order) and the like.

The dose of a conjunctive formulation may vary depending on the formulation of the novel US28 receptor modulator and/or the conjunctive agent, the subject's age, body weight, condition, and the dosage form as well as administration mode and duration. One skilled in the art would readily appreciate that the dose may vary depending on various factors as described above, and a less amount may sometimes be sufficient and an excessive amount should sometimes be required.

The conjunctive agent may be employed in any amount within the range causing no problematic side effects. The daily dose of a conjunctive agent is not limited particularly and may vary depending on the severity of the disease, the subject's age, sex, body weight and susceptibility as well as time and interval of the administration and the characteristics, preparation, type and active ingredient of the pharmaceutical formulation. An exemplary daily oral dose per kg body weight in a subject, e.g., a mammal, is about 0.001 to 2000 mg, preferably about 0.01 to 500 mg, more preferably about 0.1 to about 100 mg as medicaments, which is given usually in 1 to 4 portions.

When the novel US28 receptor modulator and a conjunctive agent are administered to a subject, the agents may be administered at the same time, but it is also possible that a conjunctive agent is first administered and then a novel US28 receptor modulator is administered, or that a novel US28 receptor modulator is first administered and then a conjunctive agent is administered. When such an intermittent administration is employed, the time interval may vary depending on the active ingredient administered, the dosage form and the administration mode, and for example, when a conjunctive agent is first administered, a novel US28 receptor modulator may be administered within 1 minute to 3 days, preferably 10 minutes to 1 day, more preferably 15 minutes to 1 hour after the administration of the conjunctive agent. When a novel US28 receptor modulator is first administered, for example, then a conjunctive agent may be administered within 1 minute to 1 day, preferably 10 minutes to 6 hours, more preferably 15 minutes to 1 hour after the administration of a novel US28 receptor modulator.

It is understood that when referring to a novel US28 receptor modulator and a conjunctive agent, it is meant a novel US28 receptor modulator alone, a conjunctive agent alone, as a part of a composition, e.g., composition, which optionally includes one or more pharmaceutical carriers. It is also contemplated that more than one conjunctive agent may be administered to the subject if desired.

1.8 EXPERIMENTAL

Solvents were distilled prior to use and melting points are uncorrected. Reagents were ordered from commercial sources and used without further purification. $^1$H NMR spectra were obtained on a 400 MHz NMR spectrometer and $^{13}$C NMR spectra were obtained at 125 MHz.

5-Bromo-2-ethoxybenzaldehyde (7a)

A mixture of 5-bromo-2-hydroxybenzaldehyde 6a (1.01 g, 5 mmol), ethyl bromide (1.09 g, 10 mmol) and potassium carbonate (1.38 g, 10 mmol) in N,N-dimethylformamide (5 mL) was stirred at room temperature for 2 days. Work up included evaporation of DMF under reduced pressure. The resultant solid was dissolved in chloroform and the organic phase was washed with 1M HCl. The chloroform layer was separated, dried over anhydrous $Na_2SO_4$, filtered and evaporated under reduced pressure to obtain a light yellow solid 7a (1.09 g, 95%). m.p. 63-64° C. $R_f$ 0.46 (15% ethyl acetate:hexane). $^1$H NMR (CDCl$_3$): δ 10.41 (s, 1H), 7.91 (s, 1H), 7.60 (dd, 1H), 6.87 (d, 1H), 4.14 (q, 2H, CH$_2$), 1.48 (t, 3H, CH$_3$); $^{13}$C NMR (CDCl$_3$): δ 188.5, 160.2, 138.2, 130.8, 126.1, 114.5, 113.3, 64.6, 14.6.

5-Chloro-2-methoxybenzaldehyde (7b)

A mixture of 5-chloro-2-hydroxybenzaldehyde 6b (940 mg, 6 mmol), iodomethane (1.14 g, 8 mmol) and potassium carbonate (1.66 g, 12 mmol) in N,N-dimethylformamide (6 mL) was stirred at room temperature for 2 days. Work up included evaporation of DMF under reduced pressure. The resultant solid was dissolved in chloroform and the organic phase was washed with 1M HCl. The chloroform layer was separated, dried over anhydrous $Na_2SO_4$, filtered and evaporated under reduced pressure to obtain yellow solid 7b (1.04 g, 96% pure, 98% yield) that was used in subsequent step without issue. m.p. 65-66° C. $R_f$ 0.34 (15% ethyl acetate:hexane). $^1$H NMR (CDCl$_3$): δ 10.41 (s, 1H), 7.78 (s, 1H), 7.49 (dd, 1H), 6.95 (d, 1H), 3.93 (s, 3H, OMe); $^{13}$C NMR (CDCl$_3$): δ 188.5, 160.3, 135.4, 128.0, 126.4, 125.6, 113.3, 56.0.

5-Chloro-2-ethoxybenzaldehyde (7c)

A mixture of 5-chloro-2-hydroxybenzaldehyde 6b (940 mg, 6 mmol), ethyl bromide (1.31 g, 12 mmol) and potassium carbonate (1.66 g, 12 mmol) in N,N-dimethylformamide (6 mL) was stirred at room temperature for 2 days. Work up included evaporation of DMF under reduced pressure. The resultant solid was dissolved in chloroform and the organic phase was washed with 1M HCl. The chloroform layer was separated, dried over anhydrous $Na_2SO_4$, filtered and evaporated under reduced pressure to obtain pure light yellow solid 7c (1.06 g, 96%). m.p. 52-54° C. $R_f$ 0.48 (15% ethyl acetate:hexane). $^1$H NMR (CDCl$_3$): δ 10.43 (s, 1H), 7.77 (s, 1H), 7.46 (dd, 1H), 6.93 (d, 1H), 4.14 (q, 2H, CH$_2$), 1.48 (t, 3H, CH$_3$); $^{13}$C NMR (CDCl$_3$): δ 188.7, 159.8, 135.4, 127.8, 126.2, 125.7, 114.1, 64.6, 14.6.

1-(2-Hydroxy-6-methoxyphenyl)ethanone (7d)

Iodomethane (2.05 g, 14 mmol) was added dropwise to a mixture of 1-(2,6-dihydroxyphenyl)ethanone 6c (2.00 g, 13 mmol) and potassium carbonate (1.99 g, 14 mmol) in N,N-dimethylformamide (13 mL) and the resulting mixture was stirred at room temperature for 2 days. Work up included evaporation of DMF under reduced pressure. The remaining solid was dissolved in chloroform and the organic phase was washed with water. The chloroform layer was separated, dried over anhydrous $Na_2SO_4$, filtered and evaporated under reduced pressure to obtain a light yellow solid (1.77 g). This crude material was purified by column chromatography (20% ethyl acetate:hexane) to obtain the product 7d (1.30 g, 60%). m.p. 50-52° C. $R_f$ 0.50 (20% ethyl acetate:hexane). $^1$H NMR (CDCl$_3$): δ 13.28 (s, 1H, OH), 7.36 (t, 1H), 6.59 (d, 1H, J=8.4 Hz), 6.41 (d, 1H, J=8.4 Hz), 3.92 (s, 3H, OCH$_3$), 2.69 (s, 3H, CH$_3$); $^{13}$C NMR (CDCl$_3$): δ 205.2, 164.7, 161.5, 136.1, 111.3, 110.7, 101.1, 55.6, 33.7.

(E)-1-(2-Hydroxyphenyl)-3-(2-methoxyphenyl)prop-2-en-1-one (8a)

2-Hydroxyacetophenone (1.02 g, 7.5 mmol), 2-methoxybenzaldehyde (1.03 g, 7.5 mmol) and MeOH (38 mL) were combined and KOH in methanol (40% weight/volume, 38 mL) added at room temperature.[20] A water condenser was attached to the flask and the yellow solution quickly turned orange upon heating and was stirred at reflux in an oil bath at 85° C. overnight. Workup involved evaporation of the solvent, addition of water and 1N HCl until the solution was at pH 1, followed by extraction with ethyl acetate (twice).[29] The organic layer was separated, dried over anhydrous $Na_2SO_4$, filtered and concentrated to give a yellow oily solid. The mixture was heated and sonicated in hexane, cooled to room temperature, and filtered to give a crude solid (1.2 g). Column chromatography was performed (20% ethyl acetate:hexane) to obtain pure product 8a (1.02 g, 54%). m.p. 101-103° C. $R_f$ 0.41 (20% ethyl acetate:hexane). $^1$H NMR (CDCl$_3$): δ 12.94 (s, 1H, OH), 8.23 (d, 1H, J=15.7 Hz), 7.93 (d, 1H), 7.79 (d, 1H, J=15.7 Hz), 7.65 (d, 1H), 7.49 (m, 1H), 7.41 (m, 1H), 7.03 (d, 1H), 6.96 (m, 3H), 3.95 (s, 3H, OMe); $^{13}$C NMR (CDCl$_3$): δ 194.3, 163.6, 159.1, 141.2, 136.2, 132.2, 129.72, 129.66, 123.7, 120.8, 120.2, 118.8, 118.6, 111.3, 55.6. 8a: Anal. $C_{16}H_{14}O_3$: C, H.

(E)-3-(5-Bromo-2-methoxyphenyl)-1-(2-hydroxyphenyl)prop-2-en-1-one (8b)

2-Hydroxy-acetophenone (1.02 g, 7.5 mmol), 5-bromo-2-anisaldehyde (1.61 g, 7.5 mmol) and MeOH (38 mL) were combined and KOH in methanol (40% weight/volume, 38 mL) was added at room temperature. A water condenser was attached to the flask and the yellow solution quickly turned orange upon heating and was stirred at reflux in oil bath at 85° C. for 2 hours. Workup involved evaporation of the solvent under reduced pressure, addition of 1N HCl until the solution was at pH 1 and extraction with ethyl acetate (twice). The organic layer was separated, dried over anhydrous $Na_2SO_4$, filtered and concentrated to give a yellow solid (2.5 g). The crude solid was heated and sonicated in hexane, then cooled down to room temperature to obtain the enriched product. Column chromatography was performed (20% ethyl acetate:hexane) to obtain pure product 8b (1.78 g, 71%). m.p. 119-121° C. $R_f$ 0.41 (20% ethyl acetate: hexane). $^1$H NMR (CDCl$_3$): δ 12.83 (s, 1H, OH), 8.14 (d, 1H, J=15.5 Hz), 7.93 (d, 1H), 7.76 (s, 1H), 7.72 (d, 1H, J=15.6 Hz), 7.50 (m, 2H), 7.03 (d, 1), 6.96 (m, 1H), 6.85 (d, 1H), 3.93 (s, 3H, OMe); $^{13}$C NMR (CDCl$_3$): δ 193.9, 163.6, 157.9, 139.2, 136.4, 134.5, 131.4, 129.8, 125.7, 121.8, 120.1, 118.9, 118.6, 113.1, 55.9. 8b: Anal. C$_{16}$H$_{13}$O$_3$Br: C, H.

(E)-3-(5-bromo-2-ethoxyphenyl)-1-(2-hydroxyphenyl)prop-2-en-1-one (8c)

2-Hydroxyacetophenone (409 mg, 3 mmol), 5-bromo-2-ethoxybenzaldehyde 7a (687 mg, 3 mmol) and MeOH (15 mL) were combined and KOH in methanol (40% weight/volume, 15 mL) was added at room temperature. A water condenser was attached to the flask and the yellow solution quickly turned orange upon heating and was stirred at reflux in an oil bath at 85° C. for 3 hours. Workup involved evaporation of the solvent under reduced pressure, addition of 1N HCl until the solution was at pH 1 and extraction with ethyl acetate (twice). Each organic layer was separated, pooled together, dried over anhydrous Na$_2$SO$_4$, filtered and concentrated to give a crude yellow solid (974 mg). Two column chromatography steps were needed to purify 8c. One column (10% ethyl acetate:hexane) was performed to remove the ketone starting material and another one (40% chloroform:hexane) to separate 8c from a cyclized byproduct. 8c was obtained as a yellow solid (438 mg, 42%). m.p. 84-86° C. $R_f$ 0.42 (10% ethyl acetate:hexane); $R_f$ 0.26 (40% chloroform:hexane); $^1$H NMR (CDCl$_3$): δ 12.84 (s, 1H, OH), 8.11 (d, 1H, J=15.6 Hz), 7.91 (d, 1H), 7.80 (d, 1H, J=15.6 Hz), 7.74 (s, 1H), 7.51 (t, 1H), 7.46 (dd, 1H), 7.03 (d, 1H), 6.95 (t, 1H), 6.89 (d, 1H), 4.14 (q, 2H, CH$_2$), 1.54 (m, 3H, CH$_3$); $^{13}$C NMR (CDCl$_3$): δ 194.0, 163.6, 157.4, 139.6, 136.4, 134.4, 132.0, 129.7, 125.6, 121.9, 120.1, 118.9, 118.6, 113.9, 112.9, 64.5, 14.8. 8c: Anal. C$_{17}$H$_{15}$O$_3$Br: C, H. HRMS for C$_{17}$H$_{15}$O$_3$Br (M+H): theory 347.0277. found 347.0354.

(E)-3-(5-bromo-2,3-dimethoxyphenyl)-1-(2-hydroxyphenyl)prop-2-en-1-one (8d)

2-Hydroxyacetophenone (300 mg, 2.2 mmol), 5-bromo-2,3-dimethoxybenzaldehyde (541 mg, 2.2 mmol) and MeOH (11 mL) were combined and KOH in methanol (40% weight/volume, 11 mL) was added at room temperature. A water condenser was attached to the flask and the yellow solution quickly turned orange upon heating and was stirred at reflux in an oil bath at 85° C. for 2 hours. Workup involved evaporation of the solvent under reduced pressure, addition of 1N HCl until the solution was at pH 1 and extraction with ethyl acetate (twice). Each organic layer was separated, pooled together, dried over anhydrous Na$_2$SO$_4$, filtered and concentrated to give a yellow solid (752 mg). The crude solid was heated and sonicated in hexane, then cooled to room temperature and filtered to obtain the majority of the pure product (315 mg). The hexane filtrate was concentrated under reduced pressure and column chromatography (20% hexane:chloroform) was performed to obtain more of the desired product. The total yield of final product 8d was 382 mg (48%). m.p. 122-124° C. $R_f$ 0.54 (20% hexane:chloroform) $^1$H NMR (CDCl$_3$): δ 12.76 (s, 1H, OH), 8.12 (d, 1H, J=15.6 Hz), 7.92 (d, 1H), 7.69 (d, 1H, J=15.6 Hz), 7.52 (t, 1H), 7.41 (s, 1), 7.09 (s, 1H), 7.04 (d, 1H), 6.96 (t, 1H), 3.89 (s, 6H, 2×OMe); $^{13}$C NMR (CDCl$_3$): δ 193.7, 163.7, 153.9, 148.3, 138.7, 136.6, 130.2, 129.8, 122.5, 122.0, 120.0, 118.9, 118.7, 117.6, 116.8, 61.5, 56.2. 8d: Anal. C$_{17}$H$_{15}$O$_4$Br.0.05H$_2$O: C, H. HRMS for C$_{17}$H$_{15}$O$_4$Br (M+H): theory 363.0226. found 363.0316.

(E)-3-(5-bromo-2,4-dimethoxyphenyl)-1-(2-hydroxyphenyl)prop-2-en-1-one (8e)

2-Hydroxyacetophenone (409 mg, 3 mmol), 5-bromo-2,4-dimethoxybenzaldehyde (735 mg, 3 mmol) and MeOH (15 mL) were combined and KOH in methanol (40% weight/volume, 15 mL) was added at room temperature. The reaction mixture was stirred at rt for 5 h. Workup involved evaporation of the solvent under reduced pressure, addition of 1N HCl until the solution was at pH 1 and extraction with ethyl acetate (twice). Each organic layer was separated, pooled together, dried over anhydrous Na$_2$SO$_4$, filtered and concentrated to give a yellow solid 8e (1.02 g, 94%). m.p. 153-157° C. $R_f$ 0.33 (40% ethyl acetate:hexane). $^1$H NMR (CDCl$_3$): δ 12.97 (s, 1H, OH), 8.15 (d, 1H, J=15.6 Hz), 7.93 (d, 1H), 7.84 (s, 1H), 7.62 (d, 1H, J=15.6 Hz), 7.49 (t, 1H), 7.02 (d, 1H), 6.95 (t, 1H), 6.49 (s, 1H), 3.98 (s, 3H, OMe), 3.96 (s, 3H, OMe); $^{13}$C NMR (CDCl$_3$): δ 193.9, 163.6, 159.9, 158.9, 139.3, 136.1, 133.0, 129.6, 120.2, 118.8 (2×C), 118.6, 117.8, 102.8, 96.1, 56.4, 56.0. 8e: Anal. C$_{17}$H$_{15}$O$_4$Br: C, H. HRMS for C$_{17}$H$_{15}$O$_4$Br (M+H): theory 363.0226. found 363.0222.

(E)-3-(5-bromo-2-methoxyphenyl)-1-(2-hydroxy-6-methoxyphenyl)prop-2-en-1-one (8f)

1-(2-Hydroxy-6-methoxyphenyl)ethanone (499 mg, 3 mmol), 5-bromo-2-methoxybenzaldehyde (645 mg, 3 mmol) and MeOH (15 mL) were combined and KOH in methanol (40% weight/volume, 15 mL) was added at room temperature. The reaction mixture was stirred at rt for 5 h. Workup involved evaporation of the solvent under reduced pressure, addition of 1N HCl until the solution was at pH 1 and extraction with ethyl acetate (twice). Each organic layer was separated, pooled together, dried over anhydrous Na$_2$SO$_4$, filtered and concentrated to give an orange solid (1.11 g). The crude solid was heated and sonicated in hexane, then cooled down to room temperature and filtered to obtain a pure orange solid 8f (560 mg, 51%). The hexane filtrate was concentrated under reduced pressure to obtain 60% pure product 8f (472 mg) that was washed with hexane again as described above and used in further reaction step without issue. m.p. 89-94° C. $R_f$ 0.31 (20% ethyl acetate: hexane) $^1$H NMR (CDCl$_3$): δ 8.06 (d, 1H, J=15.6 Hz), 7.86 (d, 1H, J=15.6 Hz), 7.71 (s, 1H), 7.46 (dd, 1H), 7.38 (t, 1H), 6.83 (d, 1H), 6.63 (d, 1H), 6.45 (d, 1H), 3.97 (s, 3H, OCH$_3$), 3.91 (s, 3H, CH$_3$); $^{13}$C NMR (CDCl$_3$): δ 194.5, 164.9, 161.0, 157.7, 136.5, 136.0, 133.8, 131.0, 129.0, 126.4, 113.0 (2×C), 112.0, 110.9, 101.6, 56.0, 55.8. 8f: Anal. C$_{17}$H$_{15}$O$_4$Br: C, H. HRMS for C$_{17}$H$_{16}$O$_4$Br (M+H): theory 363.0226. found 363.0204.

(E)-1-(2-hydroxyphenyl)-3-(5-iodo-2-methoxyphenyl)prop-2-en-1-one (8g)

2-Hydroxyacetophenone (300 mg, 2.2 mmol), 5-iodo-2-methoxybenzaldehyde (578 mg, 2.2 mmol) and MeOH (11 mL) were combined and KOH in methanol (40% weight/volume, 11 mL) was added at room temperature. A water condenser was attached to the flask and the yellow solution quickly turned orange upon heating and was stirred at reflux in an oil bath at 85° C. for 2 hours. Workup involved evaporation of the solvent under reduced pressure, addition of 1N HCl until the solution was at pH 1 and extraction with ethyl acetate (twice). Each organic layer was separated, pooled together, dried over anhydrous $Na_2SO_4$, filtered and concentrated to give a yellow solid (782 mg). The crude solid was heated and sonicated in hexane, then cooled down to room temperature and filtered to obtain the majority of the pure product (415 mg). The hexane filtrate was concentrated under reduced pressure and column chromatography (15% ethyl acetate:hexane) was performed to obtain more of the desired product. The total yield of final product 8g was 542 mg (65%). m.p. 107-109° C. $R_f$ 0.44 (15% ethyl acetate: hexane). $^1$H NMR (CDCl$_3$): δ 12.82 (s, 1H, OH), 8.10 (d, 1H, J=15.6 Hz), 7.92 (m, 2H), 7.70 (d, 1H, J=15.6 Hz), 7.66 (dd, 1H), 7.50 (dt, 1H), 7.03 (dd, 1H), 6.96 (dt, 1H), 6.73 (d, 1H), 3.92 (s, 3H, OMe); $^{13}$C NMR (CDCl$_3$): δ 193.9, 163.6, 158.6, 140.4, 139.1, 137.4, 136.4, 129.8, 126.2, 121.6, 120.1, 118.9, 118.6, 113.6, 82.9, 55.8. 8g: Anal. $C_{16}H_{15}O_3I$: C. HRMS for $C_{16}H_{15}O_3I$ (M+H): theory 380.9982. found 381.0025.

(E)-3-(5-chloro-2-methoxyphenyl)-1-(2-hydroxyphenyl)prop-2-en-1-one (8h)

2-Hydroxyacetophenone (544 mg, 4 mmol), 5-chloro-2-methoxybenzaldehyde (682 mg, 4 mmol) and MeOH (20 mL) were combined and KOH in methanol (40% weight/volume, 20 mL) was added at room temperature. A water condenser was attached to the flask and the yellow solution quickly turned orange upon heating and was stirred at reflux in an oil bath at 85° C. for 3 hours. Workup involved evaporation of the solvent under reduced pressure, addition of 1N HCl until the solution was at pH 1 and extraction with ethyl acetate (twice). Each organic layer was separated, pooled together, dried over anhydrous $Na_2SO_4$, filtered and concentrated to give a yellow solid (1.15 g). Column chromatography (10% ethyl acetate:hexane) was performed to obtain a byproduct 13h (228 mg) and the desired product 8h (372 mg, 32%). m.p. 81-82° C. $R_f$ 0.38 (10% ethyl acetate: hexane). 8h: $^1$H NMR (CDCl$_3$): δ 12.83 (s, 1H, OH), 8.15 (d, 1H, J=15.6 Hz), 7.92 (d, 1H), 7.72 (d, 1H, J=15.6 Hz), 7.61 (s, 1H), 7.51 (t, 1H), 7.35 (dd, 1H), 7.03 (d, 1H), 6.95 (t, 1H), 6.89 (d, 1H), 3.93 (s, 3H, OMe); $^{13}$C NMR (CDCl$_3$): δ 193.9, 163.6, 157.4, 139.3, 136.4, 131.5, 129.7, 128.5, 125.9, 125.1, 121.7, 120.1, 118.9, 118.6, 112.6, 56.0. 8h: Anal. $C_{16}H_{13}O_3Cl$: C, H. HRMS for $C_{16}H_{14}O_3Cl$ (M+H): theory 289.0626. found 289.0680.

(E)-3-(5-chloro-2-ethoxyphenyl)-1-(2-hydroxyphenyl)prop-2-en-1-one (8i)

2-Hydroxyacetophenone (544 mg, 4 mmol), 5-chloro-2-ethoxybenzaldehyde 7c (738 mg, 4 mmol) and MeOH (20 mL) were combined and KOH in methanol (40% weight/volume, 20 mL) was added at room temperature. The reaction mixture was stirred at rt for 5 h. Workup involved evaporation of the solvent under reduced pressure, addition of 1N HCl until the solution was at pH 1 and extraction with ethyl acetate (twice). Each organic layer was separated, pooled together, dried over anhydrous $Na_2SO_4$, filtered and concentrated to give a yellow solid (1.20 g). Column chromatography (30% chloroform:hexane) was performed to obtain the total yield of final product 8i (359 mg, 30%). m.p. 61-65° C. $R_f$ 0.25 (30% chloroform:hexane) $^1$H NMR (CDCl$_3$): δ 12.85 (s, 1H, OH), 8.10 (d, 1H, J=15.6 Hz), 7.90 (d, 1H), 7.79 (d, 1H, J=15.6 Hz), 7.58 (s, 1H), 7.50 (t, 1H), 7.31 (dd, 1H), 7.02 (d, 1H), 6.94 (t, 1H), 6.86 (d, 1H), 4.12 (q, 2H, CH$_2$), 1.53 (m, 3H, CH$_3$); $^{13}$C NMR (CDCl$_3$): δ 194.0, 163.6, 156.9, 139.6, 136.4, 131.5, 129.6, 129.1, 125.7, 125.0, 121.8, 120.1, 118.9, 118.6, 113.4, 64.5, 14.8. 8i: Anal. $C_{17}H_{15}O_3Cl$: C, H. HRMS for $C_{17}H_{15}O_3Cl$ (M+H): theory 303.0782. found 303.0744.

(E)-1-(2-hydroxyphenyl)-3-(2-methoxy-5-methylphenyl)prop-2-en-1-one (8j)

2-Hydroxyacetophenone (544 mg, 4 mmol), 2-methoxy-5-methylbenzaldehyde (601 mg, 4 mmol) and MeOH (20 mL) were combined and KOH in methanol (40% weight/volume, 20 mL) was added at room temperature. The reaction mixture was stirred at rt for 5 h. Workup involved evaporation of the solvent under reduced pressure, addition of 1N HCl until the solution was at pH 1 and extraction with ethyl acetate (twice). Each organic layer was separated, pooled together, dried over anhydrous $Na_2SO_4$, filtered and concentrated to give an orange solid (1.14 g). The crude solid was heated and sonicated in hexane, then cooled down to room temperature and filtered to obtain a yellow solid 8j (492 mg, 46%). The hexane filtrate was concentrated under reduced pressure to obtain product 8j (367 mg) that was used in further reaction step without issue. m.p. 69-72° C. $R_f$ 0.46 (20% ethyl acetate:hexane) $^1$H NMR (CDCl$_3$): δ 13.00 (s, 1H, OH), 8.23 (d, 1H, J=15.6 Hz), 7.96 (d, 1H), 7.79 (d, 1H, J=15.6 Hz), 7.51 (t, 1H), 7.47 (s, 1H), 7.23 (d, 1H), 7.05 (d, 1H), 6.97 (t, 1H), 6.88 (d, 1H), 3.94 (s, 3H, OCH$_3$), 2.36 (s, 3H, CH$_3$); $^{13}$C NMR (CDCl$_3$): δ 194.3, 163.6, 157.1, 141.3, 136.1, 132.9, 130.0, 129.9, 129.7, 123.3, 120.4, 120.2, 118.8, 118.5, 111.3, 55.7, 20.4. 8j: Anal. $C_{17}H_{16}O_3 \cdot 0.14H_2O$: C, H. HRMS for $C_{17}H_{16}O_3$ (M+H): theory 269.1172. found 269.1201.

(E)-1-(2-(Benzyloxy)-6-hydroxyphenyl)-3-(2-methoxyphenyl)prop-2-en-1-one (8k)

The O-benzyl derivative 10b (0.7 g, 2.89 mmol), 2-methoxybenzaldehyde (0.40 g, 2.94 mmol) and methanol (15 mL) were combined in a KOH in methanol solution (40% weight/volume) at room temperature. The yellow solution was stirred at reflux at 85° C. for 19 hours.[20] The dark orange solution was concentrated to remove most of the methanol and diluted with water (150 mL). The aqueous phase was extracted three times with ethyl acetate (150 mL total). The organic layer was then washed once with 1M HCl (40 mL). The organic layer was again separated, dried over anhydrous $Na_2SO_4$, filtered and concentrated to give 8k as a yellow orange solid (1.07 g crude). The crude solid was recrystallized using 25% ethyl acetate:hexane (22 mL). Chalcone 8k was obtained as an orange solid (0.63 g; 60%). $R_f$ 0.56 (25% ethyl acetate: hexane). In CDCl$_3$ two conformers were observed (3.4:1 ratio), which generated a complex spectrum, $^1$H NMR (CDCl$_3$): δ 13.49 (s, 0.77H), 8.20 (d, 1H, J=15.75 Hz), 7.90 (d, 0.8H, J=15.8 Hz), 7.88 (d, 0.2H, J=15.7 Hz), 7.48 (d, 2H), 7.42-7.24 (m, 5H), 6.91 (d, 1H), 6.85 (d, 1H), 6.71 (m, 1H), 6.65 (d, 1H), 6.53 (d, 1H), 5.14 (s, 2H), 3.80 (s, 3H, OMe). 8k: Anal. $C_{23}H_{20}O_4$: C, H.

(E)-1-(2-(Benzyloxy)-6-hydroxyphenyl)-3-(5-bromo-2-methoxyphenyl)prop-2-en-1-one (8l)

The O-benzyl derivative 10b (566 mg, 2.3 mmol), 5-bromo-2-methoxybenzaldehyde (495 mg, 2.3 mmol) and methanol (10 mL) were combined in 9.2 mL total of KOH in MeOH (40% weight/volume) at room temperature. The orange solution was stirred at reflux for 3 hours at 85° C.[20] The dark orange solution was concentrated to remove most of the methanol and then diluted with water (150 mL). The aqueous phase was extracted three times with ethyl acetate. The combined ethyl acetate layers were then washed once with 1M HCl (40 mL). The organic layer was again separated, dried over anhydrous $Na_2SO_4$, filtered and concentrated to give 8l as a crude orange solid (0.1 g). The product was collected by precipitating in 100% hexane followed by filtration and provide the pure product 8l (830 mg, 82%). m.p. 121-123° C. $R_f$ 0.49 (25% ethyl acetate: hexane). In $CDCl_3$ two conformers were noticed (2:1 ratio) which generated a complex spectrum, $^1H$ NMR ($CDCl_3$): δ 13.09 (s, 0.65H), 8.04 (d, 1H, J=15.9 Hz), 7.82 (d, 0.65H), 7.81 (d, 0.35H, J=15.7 Hz), 7.46-7.28 (m, 8H), 6.75 (d, 1H), 6.65 (d, 1H), 6.53 (d, 1H), 5.15 (5, 2H), 3.78 (5, 3H, OMe); $^{13}C$ NMR ($CDCl_3$): δ 194.7, 164.9, 160.1, 157.5, 136.3, 135.9, 135.6, 133.3, 135.9, 135.6, 133.9, 130.5, 129.0, 128.8, 128.6, 127.6, 126.1, 112.9, 112.8, 112.3, 111.2, 102.7, 71.3, 55.7. 8l: Anal. $C_{22}H_{19}O_4Br.0.05H_2O$: C, H.

(E)-3-(5-bromo-2-methoxyphenyl)-1-(1-hydroxynaphthalen-2-yl)prop-2-en-1-one (8m)

1-(1-Hydroxynaphthalen-2-yl)ethanone (559 mg, 3.0 mmol), 5-bromo-2-methoxybenzaldehyde (645 mg, 3.0 mmol) and MeOH (15 mL) were combined and KOH in methanol (40% weight/volume, 15 mL) was added at room temperature. A water condenser was attached to the flask and the yellow solution quickly turned red upon heating and was stirred at reflux in an oil bath at 85° C. for 2 hours. Workup involved evaporation of the solvent under reduced pressure, addition of 1N HCl until the solution was at pH 1 and extraction with ethyl acetate (twice). Each organic layer was separated, pooled together, dried over anhydrous $Na_2SO_4$, filtered and concentrated to give a yellow solid (1.146 g). The crude solid was heated and sonicated in hexane, then cooled down to room temperature and filtered to obtain 92% pure product (619 mg). Column chromatography (10% ethyl acetate:hexane) was performed to obtain pure 8m (565 mg, 49%). m.p. 117-127° C. $R_f$ 0.43 (10% ethyl acetate:hexane). $^1H$ NMR ($CDCl_3$): δ 14.87 (5, 1H, OH), 8.50 (d, 1H), 8.20 (d, 1H, J=15.6 Hz), 7.84 (d, 1H), 7.80 (d, 1H, J=15.6 Hz), 7.79 (5, 1H), 7.78 (d, 1H), 7.65 (dt, 1H), 7.55 (dt, 1H), 7.49 (dd, 1H), 7.32 (d, 1H), 6.85 (d, 1H), 3.94 (5, 3H, OMe); $^{13}C$ NMR ($CDCl_3$): δ 193.3, 164.5, 157.9, 138.7, 137.4, 134.3, 131.4, 130.2, 127.4, 125.9, 125.8, 125.5, 124.5, 124.0, 122.0, 118.2, 113.5, 113.1, 113.0, 55.9. 8m: $C_{20}H_{15}BrO_3$: C, H. HRMS for $C_{20}H_{16}O_3Br$ (M+H): theory 385.0259. found 385.0253.

3-Hydroxy-2-(2-methoxyphenyl)-4H-chromen-4-one (9a)

Chalcone 8a (200 mg, 0.79 mmol) was dissolved in a 3M KOH solution in 96% ethanol (5.7 mL). Then 35% $H_2O_2$ (1.7 mL) was added dropwise to the mixture cooled in an ice bath (the mixture turned viscous) and stirred for 30 minutes. The ice bath was removed and the reaction stirred at room temperature overnight. TLC (25% ethyl acetate:hexane) showed the completion of the reaction via the consumption of 8a, then the mixture was acidified to pH 1 with 1N HCl at 0° C. A precipitate formed as acid was added.[29] The flask was left in the refrigerator overnight to obtain maximal precipitations. A pure white solid 9a (109 mg, 51%) was collected by vacuum filtration. m.p. 210-212° C. $R_f$ 0.24 (25% ethyl acetate:hexane). $^1H$ NMR ($CDCl_3$): δ 8.29 (d, 1H), 7.68 (m, 1H), 7.59 (d, 1H), 7.53 (m, 1H), 7.51 (m, 1H), 7.42 (m, 1H), 7.12 (m, 1H), 7.08 (d, 1H), 6.39 (s, 1H, OH), 3.89 (s, 3H, OMe); $^{13}C$ NMR ($CDCl_3$): δ 173.3, 157.5, 156.1, 145.9, 138.8, 133.3, 132.1, 130.9, 125.5, 124.3, 121.4, 120.6, 119.7, 118.5, 111.9, 56.0. 9a: Anal. $C_{16}H_{12}O_4.0.03H_2O$: C, H.

2-(5-Bromo-2-methoxyphenyl)-3-hydroxy-4H-chromen-4-one (9b)

(E)-3-(5-Bromo-2-methoxyphenyl)-1-(2-hydroxyphenyl)prop-2-en-1-one 8b (333 mg, 1 mmol) was dissolved in a 3M KOH solution in 96% ethanol (7.3 mL). Then 35% $H_2O_2$ (2.2 mL) was added dropwise to the mixture cooled in an ice bath (the mixture turned viscous) and stirred for 30 minutes. The ice bath was removed and the reaction stirred at room temperature for 3 hours. TLC (20% ethyl acetate:hexane) showed the completion of the reaction via the consumption of 8b ($R_f$ 0.41). The mixture was then acidified to pH 1 with 1N HCl at 0° C.[29] A precipitate formed as the acid was added. The flask was stored at 4° C. overnight to obtain maximal precipitations. A light yellow solid 9b (0.22 g, 80%) was collected by vacuum filtration. m.p. 159-161° C. $R_f$ 0.22 (25% ethyl acetate: hexane) $^1H$ NMR ($CDCl_3$): δ 8.28 (d, 1H), 7.70 (m, 2H), 7.59 (d, 1H), 7.52 (m, 1H), 7.43 (m, 1H), 6.95 (d, 1H), 6.41 (s, 1H, OH), 3.87 (s, 3H, OMe); $^{13}C$ NMR ($CDCl_3$): δ 173.6, 156.7, 156.0, 144.1, 139.5, 134.4, 133.5, 133.4, 125.5, 124.4, 121.82, 121.3, 118.4, 113.7, 112.6, 56.2. 9b: Anal. $C_{16}H_{11}O_4Br.1H_2O$: C, H.

2-(5-Bromo-2-ethoxyphenyl)-3-hydroxy-4H-chromen-4-one (9c)

(E)-3-(5-bromo-2-ethoxyphenyl)-1-(2-hydroxyphenyl)prop-2-en-1-one 8c (170 mg, 0.49 mmol) was dissolved in a 3M KOH solution in 96% ethanol (3.5 mL). Then 35% $H_2O_2$ (1.1 mL) was added dropwise to the mixture cooled in an ice bath (the mixture turned viscous) and stirred for 30 minutes. The ice bath was removed and the reaction stirred at room temperature for 3 hours. TLC (10% ethyl acetate: hexane) showed the completion of the reaction via the consumption of 8c ($R_f$ 0.42). The mixture was then acidified to pH 1 with 1N HCl at 0° C. A precipitate formed as the acid was added. The flask was stored at 4° C. overnight to obtain maximal precipitations. An impure light brown solid (96 mg) was collected by vacuum filtration and further purified by column chromatography (100% chloroform) to obtain 9c as a tan solid (83 mg, 47%). m.p. 149-155° C. $R_f$ 0.40 (100% chloroform) $^1H$ NMR ($CDCl_3$): δ 8.28 (d, 1H), 7.72 (s, 1H), 7.70 (t, 1H), 7.55 (dd, 1H), 7.51 (d, 1H), 7.43 (t, 1H), 6.93 (d, 1H), 6.50 (s, 1H, OH), 4.11 (q, 2H, $CH_2$), 1.35 (t, 3H, $CH_3$); $^{13}C$ NMR ($CDCl_3$): δ 173.3, 156.0 (2×C), 144.2, 138.9, 134.5, 133.6, 133.4, 125.6, 124.5, 121.8, 121.3, 118.4, 114.6, 112.4, 64.8, 14.7. 9c: Anal. $C_{17}H_{13}O_4Br.0.1H_2O$: C, H. HRMS for $C_{17}H_{13}O_4Br$ (M+H): theory 361.0070. found 361.0139.

2-(5-Bromo-2,3-dimethoxyphenyl)-3-hydroxy-4H-chromen-4-one (9d)

(E)-3-(5-bromo-2,3-dimethoxyphenyl)-1-(2-hydroxyphenyl)prop-2-en-1-one 8d (161 mg, 0.44 mmol) was dissolved in a 3M KOH solution in 96% ethanol (3.2 mL). Then 35% $H_2O_2$ (1.0 mL) was added dropwise to the mixture cooled in an ice bath (the mixture turned viscous) and stirred for 30 minutes. The ice bath was removed and the reaction stirred at room temperature for 3 hours. TLC (20% hexane:chloroform) showed the completion of the reaction via the consumption of 8d ($R_f$ 0.54). The mixture was then acidified to pH 1 with 1N HCl at 0° C. A precipitate formed as the acid was added. The flask was stored at 4° C. overnight to obtain maximal precipitations. An impure light brown solid (98 mg) was collected by vacuum filtration and further purified by column chromatography (0.5% methanol:chloroform) to obtain 9d as a tan solid (65 mg, 39%). m.p. 153-158° C. $R_f$ 0.35 (0.5% methanol:chloroform) $^1$H NMR (CDCl$_3$): δ 8.28 (d, 1H), 7.70 (t, 1H), 7.51 (d, 1H), 7.43 (t, 1H), 7.35 (s, 1H), 7.17 (s, 1H), 6.61 (s, 1H, OH), 3.92 (s, 3H, OMe), 3.91 (s, 3H, OMe); $^{13}$C NMR (CDCl$_3$): δ 173.3, 156.0, 153.9, 146.9, 143.9, 138.9, 133.7, 126.1, 125.6, 124.7, 124.6, 121.3, 118.4, 117.8, 116.2, 61.4, 56.3. 9d: Anal. C$_{17}$H$_{13}$O$_5$Br.0.05H$_2$O: C, H. HRMS for C$_{17}$H$_{13}$O$_5$Br (M+H): theory 377.0019. found 377.0103.

2-(5-Bromo-2,4-dimethoxyphenyl)-3-hydroxy-4H-chromen-4-one (9e)

(E)-3-(5-bromo-2,4-dimethoxyphenyl)-1-(2-hydroxyphenyl)prop-2-en-1-one 8e (208 mg, 0.57 mmol) was dissolved in a 3M KOH solution in 96% ethanol (4.2 mL). Then 35% H$_2$O$_2$ (1.2 mL) was added dropwise to the mixture cooled in an ice bath (the mixture turned viscous) and stirred for 30 minutes. The ice bath was removed and the reaction stirred at room temperature for 3 hours. TLC (40% ethyl acetate:hexane) showed the completion of the reaction via the consumption of 8e ($R_f$ 0.33). The mixture was then acidified to pH 1 with 1N HCl at 0° C. A precipitate formed as the acid was added. The flask was stored at 4° C. overnight to obtain maximal precipitation. The product 9e (174 mg, 81%) was collected by vacuum filtration as a tan solid. m.p. 196-201° C. $R_f$ 0.32 (50% ethyl acetate:hexane) $^1$H NMR (CDCl$_3$): δ 8.26 (d, 1H), 7.75 (s, 1H), 7.68 (t, 1H), 7.51 (d, 1H), 7.41 (t, 1H), 6.60 (s, 1H), 6.51 (s, 1H, OH), 3.98 (s, 3H, OMe), 3.90 (s, 3H, OMe); $^{13}$C NMR (CDCl$_3$): δ 173.2, 158.6, 158.3, 156.0, 144.4, 138.8, 134.5, 133.4, 125.5, 124.4, 121.3, 118.4, 113.4, 102.2, 96.9, 56.4, 56.3. 9e: Anal. C$_{17}$H$_{13}$O$_5$Br: C, H. HRMS for C$_{17}$H$_{13}$O$_5$Br (M+H): theory 377.0019. found 377.0069.

2-(5-Bromo-2-methoxyphenyl)-3-hydroxy-5-methoxy-4H-chromen-4-one (9f)

(E)-3-(5-bromo-2-methoxyphenyl)-1-(2-hydroxy-6-methoxyphenyl)prop-2-en-1-one 8f (221 mg, 75% pure, 0.52 mmol) was dissolved in a 3M KOH solution in 96% ethanol (3.8 mL). Then 35% H$_2$O$_2$ (1.1 mL) was added dropwise to the mixture cooled in an ice bath (the mixture turned viscous) and stirred for 30 minutes. The ice bath was removed and the reaction stirred at room temperature for 3 hours. TLC (20% ethyl acetate:hexane) showed the completion of the reaction via the consumption of 8f ($R_f$ 0.31). The mixture was then acidified to pH 1 with 1N HCl at 0° C. A precipitate formed as the acid was added. The flask was stored at 4° C. overnight to obtain maximal precipitations. A yellow solid (163 mg) was collected by vacuum filtration. The crude solid was heated and sonicated in chloroform, then cooled down to room temperature and filtered to obtain 9f as a yellow solid (55 mg, 28%). m.p. 207-213° C. $R_f$ 0.29 (100% chloroform) $^1$H NMR (CDCl$_3$): δ 8.35 (d, 1H), 7.58 (t, 1H), 7.43 (dd, 1H), 7.27 (s, 1H, OH), 6.92 (d, 1H), 6.80 (d, 1H), 6.63 (d, 1H), 4.01 (s, 3H, OMe), 3.89 (s, 3H, OMe); $^{13}$C NMR (CDCl$_3$): δ 182.2, 166.9, 158.6, 157.6, 147.3, 138.4, 134.0, 133.4, 123.5, 113.1, 112.4, 110.9, 105.3, 104.9, 104.4, 56.3, 55.9; Mass spectrum for C$_{17}$H$_{13}$BrO$_5$ (M+H): theory 377, LC-MS indicated a facile loss of methyl during ionization (M=363).

3-Hydroxy-2-(5-iodo-2-methoxyphenyl)-4H-chromen-4-one (9g)

(E)-1-(2-hydroxyphenyl)-3-(5-iodo-2-methoxyphenyl)prop-2-en-1-one 8g (251 mg, 0.66 mmol) was dissolved in a 3M KOH solution in 96% ethanol (4.8 mL). Then 35% H$_2$O$_2$ (1.5 mL) was added dropwise to the mixture cooled in an ice bath (the mixture turned viscous) and stirred for 30 minutes. The ice bath was removed and the reaction stirred at room temperature for 3 hours. TLC (15% ethyl acetate:hexane) showed the completion of the reaction via the consumption of 8g ($R_f$ 0.44). The mixture was then acidified to pH 1 with 1N HCl at 0° C. A precipitate formed as the acid was added. The flask was stored at 4° C. overnight to obtain maximal precipitations. A light brown solid (173 mg) was collected by vacuum filtration and purified by column chromatography (25% ethyl acetate:hexane) to obtain 9g as a tan solid (115 mg, 44%). m.p. 153-159° C. $R_f$ 0.27 (25% ethyl acetate:hexane) $^1$H NMR (CDCl$_3$): δ 8.27 (d, 1H), 7.85 (s, 1H), 7.76 (dd, 1H), 7.69 (t, 1H), 7.52 (d, 1H), 7.42 (t, 1H), 6.84 (d, 1H), 6.42 (s, 1H, OH), 3.86 (s, 3H, OMe); $^{13}$C NMR (CDCl$_3$): δ 173.2, 157.4, 156.0, 143.9, 140.5, 139.1, 138.9, 133.5, 125.6, 124.5, 122.1, 121.2, 118.5, 114.1, 82.2, 56.1. 9g: Anal. C$_{16}$H$_{11}$O$_4$I: C, H. HRMS for C$_{16}$H$_{11}$O$_4$I (M+H): theory 394.9775. found 394.9851.

2-(5-chloro-2-methoxyphenyl)-3-hydroxy-4H-chromen-4-one (9h)

(E)-3-(5-chloro-2-methoxyphenyl)-1-(2-hydroxyphenyl)prop-2-en-1-one 8h (221 mg, 0.77 mmol) was dissolved in a 3M KOH solution in 96% ethanol (5.9 mL). Then 35% H$_2$O$_2$ (1.6 mL) was added dropwise to the mixture cooled in an ice bath (the mixture turned viscous) and stirred for 30 minutes. The ice bath was removed and the reaction stirred at room temperature for 3 hours. TLC (10% ethyl acetate:hexane) showed the completion of the reaction via the consumption of 8h ($R_f$ 0.38). The mixture was then acidified to pH 1 with 1N HCl at 0° C. A precipitate formed as the acid was added. The flask was stored at 4° C. overnight to obtain maximal precipitation. A light pink solid 9h (114 mg, 49%) was collected by vacuum filtration. m.p. 160-167° C. $R_f$ 0.33 (100% chloroform) $^1$H NMR (CDCl$_3$): δ 8.28 (d, 1H), 7.69 (t, 1H), 7.57 (s, 1H), 7.52 (d, 1H), 7.44 (dd, 1H), 7.43 (t, 1H), 7.00 (d, 1H), 6.46 (s, 1H, OH), 3.87 (s, 3H, OMe); $^{13}$C NMR (CDCl$_3$): δ 173.3, 156.1, 156.0, 144.1, 139.0, 133.6, 131.6, 130.6, 125.6 (2×C), 124.5, 121.3, 121.1, 118.5, 113.2, 56.3. 9h: Anal. C$_{16}$H$_{11}$O$_4$Cl: C, H. HRMS for C$_{16}$H$_{11}$O$_4$Cl (M+H): theory 303.0419. found 303.0488.

2-(5-chloro-2-ethoxyphenyl)-3-hydroxy-4H-chromen-4-one (9i)

(E)-3-(5-chloro-2-ethoxyphenyl)-1-(2-hydroxyphenyl)prop-2-en-1-one 8i (178 mg, 0.59 mmol) was dissolved in a 3M KOH solution in 96% ethanol (4.3 mL). Then 35% H$_2$O$_2$ (1.2 mL) was added dropwise to the mixture cooled in an ice bath (the mixture turned viscous) and stirred for 30 minutes. The ice bath was removed and the reaction stirred at room temperature for 3 hours. TLC (30% chloroform:hexane) showed the completion of the reaction via the consumption of 8i ($R_f$ 0.25). The mixture was the acidified to pH 1 with 1N HCl at 0° C. A precipitate formed as the acid was added. The flask was stored at 4° C. overnight to obtain maximal precipitation. A crude solid (147 mg) was collected by vacuum filtration and purified by column chromatography (100% CHCl$_3$) to obtain 9i as a light yellow (112 mg, 60%).

m.p. 156-159° C. $R_f$ 0.34 (100% CHCl$_3$) $^1$H NMR (CDCl$_3$): δ 8.21 (d, 1H), 7.61 (t, 1H), 7.51 (d, 1H), 7.43 (t, 1H), 7.37-7.31 (m, 2H), 6.90 (d, 1H), 6.50 (s, 1H, OH), 4.04 (q, 2H, CH$_2$), 1.27 (t, 3H, CH$_3$); $^{13}$C NMR (CDCl$_3$): δ 172.4, 155.1, 154.6, 143.4, 138.0, 132.6, 130.6, 129.7, 124.6, 124.5, 123.5, 120.4, 120.3, 117.4, 113.2, 63.9, 13.8. 9i: Anal. C$_{17}$H$_{13}$O$_4$Cl: C, H. HRMS for C$_{17}$H$_{13}$O$_4$Cl (M+H): theory 317.0575. found 317.0613.

3-hydroxy-2-(2-methoxy-5-methylphenyl)-4H-chromen-4-one (9j)

(E)-1-(2-hydroxyphenyl)-3-(2-methoxy-5-methylphenyl)prop-2-en-1-one 8j (346 mg, 90% pure, 1.29 mmol) was dissolved in a 3M KOH solution in 96% ethanol (9.4 mL). Then 35% H$_2$O$_2$ (2.6 mL) was added dropwise to the mixture cooled in an ice bath (the mixture turned viscous) and stirred for 30 minutes. The ice bath was removed and the reaction stirred at room temperature for 3 hours. TLC (20% ethyl acetate:hexane) showed the completion of the reaction via the consumption of 8j ($R_f$ 0.46). The mixture was then acidified to pH 1 with 1N HCl at 0° C. A precipitate formed as the acid was added. The flask was stored at 4° C. overnight to obtain maximal precipitations. A light brown solid 9j (259 mg, 71%) was collected by vacuum filtration. m.p. 158-164° C. $R_f$ 0.32 (20% ethyl acetate:hexane) $^1$H NMR (CDCl$_3$): δ 8.28 (dd, 1H), 7.68 (dt, 1H), 7.52 (d, 1H), 7.41 (dt, 1H), 7.39 (d, 1H), 7.30 (dd, 1H), 6.98 (d, 1H), 6.44 (s, 1H, OH), 3.86 (s, 3H, OMe), 2.37 (s, 3H, Me); $^{13}$C NMR (CDCl$_3$): δ 173.3, 156.0, 155.4, 146.3, 138.8, 133.3, 132.6, 131.2, 130.0, 125.5, 124.3, 121.5, 119.5, 118.5, 112.0, 56.1, 20.4. 9j: Anal. C$_{17}$H$_{14}$O$_4$: C, H. HRMS for C$_{17}$H$_{15}$O$_4$ (M+H): theory 283.0965. found 283.0945.

2-Benzoxy-6-hydroxyacetophenone (10b).[30]

To a solution containing 2,6-dihydroxyacetophenone 10a (5 g, 33 mmol) in acetone (50 mL) were added benzyl bromide (6.65 g, 4.6 mL, 40.0 mmol), KI (9 g, 53 mmol), and K$_2$CO$_3$ (15 g, 106 mmol). The reaction mixture was heated to reflux overnight under a N$_2$ atmosphere, then cooled and filtered.[31] The filtrate was concentrated under reduced pressure, and the residue was redissolved in ethyl acetate, and washed with H$_2$O (50 mL). The water layer was washed three times with ethyl acetate. The organic layers were combined, dried over anhydrous MgSO$_4$, filtered and concentrated under reduced pressure to give a crude solid (12 g). The solid was purified by flash chromatography (20% ethylacetate/hexane) on a silica gel column (700 g silica). Elution with 20% ethyl acetate and hexane gave recovered starting material 10a (0.65 g) and the desired product 10b (4.0 g) as a light yellow solid. Taking into account, the recovered starting material, the yield of 10b was 58%. $R_f$ 0.52 (3:1 hexanes: ethyl acetate). $^1$H NMR (CDCl$_3$): δ 13.29 (s, 1H), 7.37 (m, 6H), 6.59 (d, 1H, J=8.4 Hz), 6.46 (d, 1H, J=8.4 Hz), 5.13 (s, 2H), 2.62 (s, 3H); matched lit spectrum.[28]

5-(Benzyloxy)-2-(2-methoxyphenyl)-4H-chromen-4-one (11a)

Ketone 8k (550 mg, 1.53 mmol) was dissolved in DMSO (100 mL) and iodine (38 mg, 0.15 mmol) was added. The mixture was heated to 140° C. and stirred overnight with a water condenser and drying tube attached. The light yellow solution was cooled and 1M HCl added until the solution turned permanently cloudy, followed by extraction with ethyl acetate three times.[20] The organic layers were pooled, and washed once with brine. The organic layer was separated, dried over anhydrous Na$_2$SO$_4$, filtered and concentrated to give crude 11a (1.05 g). The solid residue was recrystallized from ethyl acetate/hexane (1:3 by volume) overnight to give pure 11a (380 mg; 70%, from 1$^{st}$ crop). The filtrate was concentrated and a 2$^{nd}$ crop obtained (56 mg; using 20% Ethyl acetate: hexane). Total yield of 11a: 436 mg; 80%. $R_f$ 0.10 (20% ethyl acetate: hexane). $^1$H NMR (CDCl$_3$): δ 7.90 (d, 1H), 7.65 (d, 2H), 7.55-7.42 (m, 2H), 7.40 (m, 2H), 7.30 (m, 1H), 7.26 (s, 1H), 7.15-7.05 (m, 3H), 7.04 (d, 1H), 6.84 (d, 1H), 5.30 (s, 2H), 3.93 (s, 3H, OMe). $^{13}$C NMR (CDCl$_3$): δ 178.6, 158.53, 158.50, 158.47, 158.01, 136.7, 133.4, 132.2, 129.1, 128.5, 127.6, 126.6, 120.7, 120.5, 115.1, 114.3, 111.7, 110.5, 108.3, 70.9, 55.6. 11a: Anal. C$_{23}$H$_{18}$O$_4$·0.04H$_2$O: C, H.

5-(Benzyloxy)-2-(5-bromo-2-methoxyphenyl)-4H-chromen-4-one (11b)

Bromo-chalcone 8l (439 mg, 1 mmol) was dissolved in DMSO (67 mL) and Iodine (25 mg) was added to the mixture at room temperature. The mixture was refluxed at 140° C. for 3 hours. The flask was cooled to room temperature. Work up involved adding 1M HCl until the solution reached pH 1, followed by extraction with ethyl acetate (three times).[20] The organic layer was washed once with brine, separated, and dried over anhydrous Na$_2$SO$_4$, filtered and concentrated to give a crude solid. Column chromatography was performed (1:1 ethyl acetate and hexane) to give pure product 11b (0.24 g, 55%). m.p. 153-155° C. $R_f$ 0.38 (50% ethyl acetate: hexane). $^1$H NMR (CDCl$_3$): δ 8.02 (s, 1H), 7.65 (d, 2H), 7.54 (m, 2H), 7.40 (m, 2H), 7.31 (d, 1H), 7.13 (d, 1H), 7.08 (s, 1H), 6.92 (d, 1H), 6.85 (d, 1H), 5.30 (s, 2H), 3.93 (s, 3H, OMe); $^{13}$C NMR (CDCl$_3$): δ 178.4, 158.5, 158.4, 157.1, 156.7, 136.6, 134.5, 133.6, 131.5, 128.6, 127.6, 126.6, 122.3, 114.8, 113.5, 113.1, 110.5, 108.4, 70.9, 56.0. 11b: Anal. C$_{23}$H$_{17}$O$_4$Br·0.06H$_2$O: C, H.

2-(2-Methoxyphenyl)-4H-chromen-4-one (11c)

Chalcone 8a (150 mg, 0.59 mmol) was dissolved in DMSO (39 mL) and iodine (14.4 mg, 0.06 mmol) was added. The mixture was refluxed in DMSO via an oil bath at 140° C. overnight.[20] The orange solution was cooled to room temperature and 1M HCl was added until the solution pH was 1, followed by extraction with ethyl acetate four times. The organic layers were pooled, washed once with brine, dried over anhydrous Na$_2$SO$_4$, filtered and concentrated under reduced pressure to give a crude solid. The solid residue was recrystallized from ethyl acetate/hexane (1:3) overnight to give a solid (180 mg). Column chromatography was performed (25% ethyl acetate: hexane) to provide pure 11c (104 mg, 70%). m.p. 93-94° C. $R_f$ 0.12 (25% ethyl acetate: hexane). $^1$H NMR (CDCl$_3$): δ 8.24 (d, 1H), 7.91 (d, 1H), 7.68 (m, 1H), 7.54 (d, 1H), 7.49 (m, 1H), 7.41 (m, 1H), 7.15 (s, 1H), 7.12 (m, 1H), 7.06 (d, 1H), 3.95 (s, 3H, OMe); $^{13}$C NMR (CDCl$_3$): δ 178.9, 160.9, 158.0, 156.5, 133.5, 132.4, 129.3, 125.7, 124.9, 123.9, 120.9, 120.7, 118.0, 112.7, 111.8, 55.7. 11c: Anal. C$_{16}$H$_{12}$O$_3$·0.05H$_2$O: C, H.

2-(5-Bromo-2-methoxyphenyl)-4H-chromen-4-one (11d)

Bromo-chalcone 8b (250 mg, 0.75 mmol) was dissolved in DMSO (50 mL) and iodine (18.7 mg, 0.07 mmol) was added. The mixture was refluxed in DMSO via an oil bath at 140° C. for 4 hours.[20] The orange solution was cooled to room temperature and 1M HCl was added until the solution pH was 1, followed by extraction with ethyl acetate four times. The organic layers were pooled, washed once with brine, dried over anhydrous $Na_2SO_4$, filtered and concentrated under reduced pressure to give a crude solid. Column chromatography was performed (25% ethyl acetate: hexane) to provide pure product 11d (240 mg, 95% yield). m.p. 161-164° C. $R_f$ 0.12 (25% ethyl acetate: hexane). $^1$H NMR ($CDCl_3$): δ 8.23 (d, 1H), 8.04 (s, 1H), 7.70 (m, 1H), 7.57 (m, 2H), 7.42 (m, 1H), 7.15 (s, 1H), 6.94 (d, 1H), 3.94 (s, 3H, OMe); $^{13}$C NMR ($CDCl_3$): δ 178.7, 159.0, 157.1, 156.4, 134.8, 133.8, 131.7, 125.7, 125.1, 123.8, 122.6, 118.1, 113.6, 113.13, 113.10, 56.0. 11d: Anal. $C_{16}H_{11}O_3Br.0.17H_2O$: C, H.

5-Hydroxy-2-(2-methoxyphenyl)-4H-chromen-4-one (12a)

Flavone 11a (321 mg, 0.89 mmol) was dissolved in a solution of acetic acid (34 mL) and water (8.5 mL) at room temperature. The system was then attached to a water condenser and refluxed at 110° C. for 24 h.[21] The solvent was removed under reduced pressure, and the residue was heated and sonicated in hexane, and filtered to give a crude solid (201 mg). Column chromatography was performed (20% ethyl acetate:hexane) to obtain pure product 12a (162 mg, 67%). m.p. 128-130° C. $R_f$ 0.31 (20% ethyl acetate: hexane). $^1$H NMR ($CDCl_3$): δ 12.69 (s, 1H, OH), 7.91 (d, 1H), 7.52 (m, 2H), 7.12 (m, 1H), 7.11 (s, 1H), 7.06 (d, 1H), 6.98 (m, 1H), 6.80 (d, 1H), 3.95 (s, 3H, OMe); $^{13}$C NMR ($CDCl_3$): δ 184.0, 161.9, 160.8, 158.2, 156.7, 135.2, 132.9, 129.3, 120.8, 120.3, 111.8, 111.2, 110.8, 107.0, 55.7. 12a: Anal. $C_{16}H_{12}O_4$: C, H.

2-(5-Bromo-2-methoxyphenyl)-5-hydroxy-4H-chromen-4-one (12b)

Bromo-flavone 11b (100 mg, 0.23 mmol) was dissolved in a solution of acetic acid (11.3 mL) and water (2.82 mL) at room temperature. The system was then attached to a water condenser and refluxed at 110° C. for 24 h.[21] The solvent was removed under reduced pressure and column chromatography was performed (20% ethyl acetate:hexane) to obtain the pure product 12b (55 mg, 70%). m.p. 175-180° C. $R_f$ 0.28 (20% ethyl acetate: hexane). $^1$H NMR ($CDCl_3$): δ 12.57 (s, 1H, OH), 8.02 (s, 1H), 7.56 (m, 2H), 7.10 (s, 1H), 7.00 (m, 1H), 6.95 (d, 1H), 6.82 (d, 1H), 3.94 (s, 3H, OMe); $^{13}$C NMR ($CDCl_3$): δ 183.9, 160.7, 160.1, 157.2, 156.5, 135.4, 135.3, 131.8, 121.9, 113.6, 113.2, 111.7, 111.2, 110.8, 107.0, 56.1. 12b: Anal. $C_{16}H_{11}BrO_4$: C, H.

2-(5-Bromo-2-methoxyphenyl)chroman-4-one (13b)

Bromo-chalcone 8b (600 mg, 1.8 mmol) and sodium acetate (1.48 g, 18 mmol) were added together in 1-butanol (18 mL). The mixture was refluxed at 118° C. (with a reflux condenser and a drying tube attached) for a week. The mixture was then cooled to room temperature.[22] The volatiles were removed under reduced pressure, water was added and the mixture was extracted three times with $CH_2Cl_2$. The organic layer was separated, washed once with brine, separated and dried over anhydrous $Na_2SO_4$, filtered and concentrated to give a yellow oily solid. Column chromatography was performed (40% hexane: chloroform) to give pure product 13b (0.18g, 11%). m.p. 101-103° C. $R_f$ 0.73 (40% hexane: chloroform). $^1$H NMR ($CDCl_3$): δ 7.94 (d, 1H), 7.78 (s, 1H), 7.53 (m, 1H), 7.44 (d, 1H), 7.07 (m, 2H), 6.80 (d, 1H), 5.78 (d, 1H), 3.83 (s, 3H, OMe), 3.02-2.78 (m, 2H); $^{13}$C NMR ($CDCl_3$): δ 192.2, 161.7, 154.7, 136.1, 131.9, 129.8, 129.3, 127.1, 121.7, 121.0, 118.1, 113.3, 112.3, 74.2, 55.7, 43.6. 13b: Anal. $C_{16}H_{13}O_3Sr$: C, H.

2-(5-Chloro-2-methoxyphenyl)chroman-4-one (13h)

This byproduct was isolated (228 mg, 20%) during the synthesis of compound 8h (see 8h for details). m.p. 51-60° C. $R_f$ 0.36 (10% ethyl acetate:hexane). 13h: $^1$H NMR ($CDCl_3$): δ 7.87 (d, 1H), 7.57 (d, 1H), 7.45 (t, 1H), 7.22 (dd, 1H), 7.01 (d, 1H), 7.00 (t, 1H), 6.77 (d, 1H), 5.71 (dd, 1H), 3.76 (s, 3H, OMe), 2.91 (dd, 1H), 2.76 (dd, 1H); $^{13}$C NMR ($CDCl_3$): δ 192.2, 161.7, 154.2, 136.2, 129.4, 128.9, 127.1, 126.5, 126.1, 121.7, 121.0, 118.1, 111.8, 74.3, 55.7, 43.6. 13h: Anal. $C_{16}H_{13}O_3Cl$: C, H. HRMS for $C_{16}H_{14}O_3Cl$ (M+H): theory 289.0626. found 289.0639.

(E)-3-(5-Bromo-2-methoxyphenyl)acrylic acid (15)

The starting chalcone 8m ((E)-3-(5-bromo-2-methoxyphenyl)-1-(1-hydroxynaphthalen-2-yl)prop-2-en-1-one, 316 mg, 0.82 mmol) was combined with 40% KOH in EtOH (6.1 mL) and 30% $H_2O_2$ (1.8 mL) and stirred for 30 min at 0° C. and then at rt for an additional 3 h. Aqueous acid (1M HCl) was added to give a pH of 1 and the resultant precipitation was stored at 4° C. overnight and then collected by filtration and dried to give the crude cinnamic acid derivative 15 as an orange solid (157 mg, 74%). $^1$H NMR ($d_6$-DMSO): δ 12.42 (br s, 1H, OOOH), 7.88 (d, 1H, J=2 Hz), 7.73 (d, 1H, β-vinyl CH, J=16 Hz), 7.55 (dd, 1H, J=8.9 Hz and 2 Hz), 7.06 (d, 1H, J=8.9 Hz), 6.59 (d, 1H, J=16 Hz), 3.86 (s, 3H, $OCH_3$). $^{13}$C NMR ($d_6$-DMSO): δ 167.5, 156.8, 136.9, 133.8, 130.4, 124.7, 120.8, 114.0, 112.3, 56.0. $R_f$ (1% MeOH in $CHCl_3$)= 0.4.

1.9 ELEMENTAL ANALYSIS

8a: Anal. Chem theory for $C_{16}H_{14}O_3$: C: 75.57, H: 5.55. found C: 75.60, H: 5.49.
8b: Anal. Chem. Theory for $C_{16}H_{13}O_3Br$: C: 57.68, H: 3.93. Found C: 57.73, H: 3.91.
8c: Anal. Chem. theory for $C_{17}H_{15}O_3Br$: C: 58.81, H: 4.35. found C: 58.65, H: 4.24.
8d: Anal. Chem. theory for $C_{17}H_{15}O_4Br.0.05H_2O$: C: 55.47, H: 4.14. found C: 55.27, H: 4.00.
8e: Anal. Chem. theory for $C_{17}H_{15}O_4Br$: C: 56.22, H: 4.16. found C: 55.94, H: 4.09.
8f: Anal. Chem. theory for $C_{17}H_{15}O_4Br$: C: 56.22, H: 4.16. found C: 56.08, H: 3.99.
8g: Anal. Chem. theory for $C_{16}H_{15}O_3I$: C: 50.55, H: 3.45. found C: 50.54, H: 3.40.
8h: Anal. Chem. theory for $C_{16}H_{13}O_3Cl$: C: 66.56, H: 4.54. found C: 66.28, H: 4.64.
8i: Anal. Chem. theory for $C_{17}H_{15}O_3Cl$: C: 67.44, H: 4.99. found C: 67.21, H: 4.89.
8j: Anal. Chem. theory for $C_{17}H_{16}O_3.0.14H_2O$: C: 72.40, H: 5.82. found C: 72.26, H: 6.17.
8k: Anal. Chem. Theory for $C_{23}H_{20}O_4$: C: 76.65, H: 5.59. found C: 76.67, H: 5.69.
8l: Anal. Chem. Theory for $C_{22}H_{19}O_4Br.0.05H_2O$: C: 62.19, H: 4.33. found C: 62.21, H: 4.38.
8m: Anal. Chem. theory for $C_{20}H_{15}BrO_3$: C: 62.68, H: 3.95. found C: 62.94, H: 3.79.
9a: Anal. Chem theory for $C_{16}H_{12}O_4.0.03H_2O$: C: 70.86, H: 4.48. found C: 70.70, H: 4.44.

9b: Anal. Chem theory for $C_{16}H_{11}O_4Br.1H_2O$: C: 43.17, H: 2.94. found C: 43.12, H: 2.60.
9c: Anal. Chem. theory for $C_{17}H_{13}O_4Br.0.1H2O$: C: 55.04, H: 3.59. found C: 54.87, H: 3.60.
9d: Anal. Chem. theory for $C_{17}H_{13}O_5Br.0.05H2O$: C: 53.44, H: 3.46. found C: 53.14, H: 3.39.
9e: Anal. Chem. theory for $C_{17}H_{13}O_5Br$: C: 54.13, H: 3.47. found C: 54.10, H: 3.39.
9g: Anal. Chem. theory for $C_{16}H_{11}O_4I$: C: 48.75, H: 2.81. found C: 48.49, H: 2.58.
9h: Anal. Chem. theory for $C_{16}H_{11}O_4Cl$: C: 63.48, H: 3.66. found C: 63.39, H: 3.59.
9i: Anal. Chem. theory for $C_{17}H_{13}O_4Cl$: C: 64.46, H: 4.14. found C: 64.25, H: 4.03.
9j: Anal. Chem. theory for $C_{17}H_{14}O_4$: C: 72.33, H: 5.00. found C: 72.06, H: 4.96. S78
11a: Anal. Chem. Theory for $C_{23}H_{18}O_4.0.04H_2O$: C: 76.25, H: 5.03. found C: 76.18, H: 4.92.
11b: Anal. Chem theory for $C_{23}H_{17}O_4Br.0.06H_2O$: C: 62.33, H: 3.89. found C: 62.29, H: 3.94.
11c: Anal. Chem. theory for $C_{16}H_{12}O_3.0.05H_2O$: C: 74.72, H: 4.74. found C: 74.73, H: 4.73.
11d: Anal. Chem theory for $C_{16}H_{11}O_3Br.0.17H_2O$: C: 55.25, H: 3.28. found C: 55.28, H: 3.26.
12a: Anal. Chem. theory for $C_{16}H_{12}O_4$: C: 71.64, H: 4.51. found C: 71.39, H: 4.65.
12b: Anal. Chem. theory for $C_{16}H_{11}BrO_4$: C: 55.36, H: 3.19. found C: 55.09, H: 3.24
13b: Anal. Chem theory for $C_{16}H_{13}O_3Br$: C: 57.68, H: 3.93. found C: 57.56, H: 3.88.
13h: Anal. Chem. theory for $C_{16}H_{13}O_3Cl$: C: 66.56, H: 4.54. found C: 66.38, H: 4.45.

1.10 REFERENCES

All references set forth herein in this document are incorporated by reference herein to the extent that the subject matter therein does not conflict with the existing disclosure.

1. a) Dimmock, J. R.; Elias, D. W.; Beazely, M. A.; Kandepu, N. M., Bioactivities of chalcones. Curr Med Chem 1999, 6, 1125-1149; b) Sahu, N. K.; Balbhadra, S. S.; Choudhary, J.; Kohli, D. V. Exploring Pharmacological Significance of Chalcone Scaffold: A Review. Curr. Med. Chem. 2012, 19, 209-225.
2. Lin, Y. M.; Zhou, Y.; Flavin, M. T.; Zhou, L. M.; Niea, W.; Chenb, F. C., Chalcones and Flavonoids as Anti-Tuberculosis Agents. Bioorg Med Chem 2002, 10, 2795-2802.
3. Babu, M. A.; Shakya, N.; Prathipati, P.; Kaskhedikar, S. G.; Saxena, A. K., development of 3D-QSAR Models for 5-Lipoxygenase Antagonists: Chalcones. Bioorg Med Chem 2002, 10, 4035-4041.
4. Sogawa, S.; Nihro, Y.; Ueda, H.; Izumi, A.; Miki, T.; Matsumoto, H.; Satoh, T., 3,4-Dihydroxychalcones as Potent 5-Lipoxygenase and Cyclooxygenase Inhibitors. J Med Chem 1993, 36, 3904-3909.
5. Zhao, F.; Zhao, Q. J.; Zhang, D. Z.; Jin, Y. S.; Zhang, W., Synthesis and Protein Tyrosine Phosphatase 1B-Inhibitory Activity of Chalcones. Asian J Chem 2011, 23, 5339-5342.
6. Buckwold, V.; Wilson, R.; Nalca, A.; Beer, B.; Voss, T.; Turpin, J.; Buckheit, R.; Wei, J.; Wenzelmathers, M.; Walton, E., Antiviral activity of hop constituents against a series of DNA and RNA viruses. Antiviral Res 2004, 61, 57-62.
7. Wang, Y.; Chen, Y.; Wang, J.; Chen, J.; Aggarwal, B. B.; Pang, X.; Liu, M., Xanthohumol, a Prenylated Chalcone Derived from Hops, Suppresses Cancer Cell Invasion through Inhibiting the Expression of CXCR4 Chemokine Receptor. Curr Mol Med 2012, 12, 153-162.
8. Chua, A. W.; Hay, H. S.; Rajendran, P.; Shanmugam, M. K.; Li, F.; Bist, P.; Koay, E. S.; Lim, L. H.; Kumar, A. P.; Sethi, G., Butein downregulates chemokine receptor CXCR4 expression and function through suppression of NF-kappaB activation in breast and pancreatic tumor cells. Biochem Pharmacol 2010, 80, 1553-1562.
9. Evers, D.; Chao, C.; Wang, X.; Zhang, Z.; Huong. S.; Huang, E., Human cytomegalovirus-inhibitory flavonoids: Studies on antiviral activity and mechanism of action. Antiviral Research 2005, 68, 124-134.
10. Kim, H J.; Woo, E R.; Shin, C G.; Park, H. A new flavonol glycoside gallate ester from Acer okamotoanum and its inhibitory activity against human immunodeficiency virus-1 (HIV-10 integrase. J Nat Prod. 1998, 61, 145-148.
11. Hachet-Haas, M.; Balabanian, K.; Rohmer, F.; Pons, F.; Franchet, C.; Lecat, S.; Chow, K. Y.; Dagher, R.; Gizzi, P.; Didier, B.; Lagane, B.; Kellenberger, E.; Bonnet, D.; Baleux, F.; Haiech, J.; Parmentier, M.; Frossard, N.; Arenzana-Seisdedos, F.; Hibert, M.; Galzi, J. L., Small neutralizing molecules to inhibit actions of the chemokine CXCL12. J Biol Chem 2008, 283, 23189-23199.
12. Gao, J. L.; Murphy, P. M., Human Cytomegalovirus Open Reading Frame US28 Encodes a Functional Beta Chemokine Receptor. J Biol Chem 1994, 269, 28539-28542.
13. Kralj, A.; Wetzel, A.; Mahmoudian, S.; Stamminger, T.; Tschammer, N.; Heinrich, M. R., Identification of novel allosteric modulators for the G-protein coupled US28 receptor of human cytomegalovirus. Bioorg Med Chem Lett 2011, 21, 5446-5450.
14. Boomker, J. M.; van Luyn, M. J.; The, T. H.; de Leij, L. F.; Harmsen, M. C., US28 actions in HCMV infection: lessons from a versatile hijacker. Rev Med Virol 2005, 15, 269-282.
15. Sodhi, A.; Montaner, S.; Gutkind, J. S., Viral hijacking of G-protein-coupled-receptor signalling networks. Nat Rev Mol Cell Biol 2004, 5, 998-1012.
16. Maussang, D.; Vischer, H. F.; Leurs, R.; Smit, M. J., Herpesvirus-encoded G protein-coupled receptors as modulators of cellular function. Mol Pharmacol 2009, 76, 692-701.
17. Vomaske, J.; Nelson, J. A.; Streblow, D. N., Human Cytomegalovirus US28: A Functionally Selective Chemokine Binding Receptor. Infect Disord Drug Targets 2009, 9, 548-556.
18. Maussang, D.; Verzijl, D.; van Walsum, M.; Leurs, R.; Holl, J.; Pleskoff, 0.; Michel, D.; van Dongen, G. A.; Smit, M. J., Human cytomegalovirus-encoded chemokine receptor US28 promotes tumorigenesis. Proc Natl Acad Sci USA 2006, 103, 13068-13073.
19. Tschammer, N. Virally Encoded G protein-Coupled Receptors: Overlooked Therapeutic Opportunities? Annual Reports in Medicinal Chemistry 2012, 47, 379-392.
20. Jeffrey A. Smith, David J. Maloney, Sidney M. Hecht and Deborah A. Lannigan, Structural basis for the activity of the RSK-specific inhibitor, SL0101. Bioorganic & Medicinal Chemistry, 2007, 15, 5018-5034.
21. Kazuaki Yamasaki; Ryogo Hishiki; Eisuke Kato; Jun Kawabata. Study of Kaempferol Glycoside as an Insulin Mimic Reveals Glycon to be the Key Active Structure, ACS Med. Chem. Lett. 2011, 2, 17-21.

22. Chimenti, J. A. A new series of flavones, thioflavones, and flavanones as selective monoamine oxidase-B inhibitors. Bioorganic & Medicinal Chemistry, 2010, 18, 1273-1279.
23. PathDetect in Vivo Signal Transduction Pathway trans-Reporting Systems, Instruction Manual, Agilent Technologies, Inc., 2011; 219000-12, Revision B.
24. Bright-Glo™ Luciferase Assay System, Technical Manual, Promega Corporation, Madison, Wis., September 2011; Part# TM052.
25. a) Phanstiel I V, O.; Kaur, N.; Delcros, J.-G. Structure-activity investigations of polyamine-anthracene conjugates and their uptake via the polyamine transporter. Amino Acids 2007, 33, 305-313; b). Parisini, E.; Metrangolo, P.; Pilati, T.; Resnati, G.; Terraneo, G. Halogen bonding in halo-carbon-protein complexes: a structural survey. Chem. Soc. Rev. 2011, 40, 2267-2278.
26. Hesselgesser, J.; Ng, H. P.; Liang, M.; Zheng, W.; May, K.; Bauman, J. G.; Monahan, S.; Islam, I.; Wei, G. P.; Ghannam, A.; Taub, D. D.; Rosser, M.; Snider, R. M.; Morrissey, M. M.; Perez, H. D.; Horuk, R., Identification and Characterization of Small Molecule Functional Antagonists of the CCR1 Chemokine Receptor. J Biol Chem 1998, 273, 15687-15692
27. Vischer, H. F.; Hulshof, J. W.; Hulscher, S.; Fratantoni, S. A.; Verheij, M. H.; Victorina, J.; Smit, M. J.; de Esch, I. J.; Leurs, R., Identification of novel allosteric nonpeptidergic inhibitors of the human cytomegalovirus-encoded chemokine receptor US28. Bioorg Med Chem 2010, 18, 675-688.
28. Casarosa, P.; Menge, W. M.; Minisini, R.; Otto, C.; van Heteren, J.; Jongejan, A.; Timmerman, H.; Moepps, B.; Kirchhoff, F.; Mertens, T.; Smit, M. J.; Leurs, R., Identification of the first nonpeptidergic inverse agonist for a constitutively active viral-encoded G protein-coupled receptor. J Biol Chem 2003, 278, 5172-5178.
29. Chan, K. F.; Zhao, Y.; Chow, T. W. C.; Yan, C. S. W.; Ma, D. K.; Burkett, B. A.; Wong, I. L. K; Chow, L. M. C.; Chan, T. H. Flavonoid Dimers as Bivalent modulators for P-Glycoprotein-Based Multidrug Resistance: Structure-Activity Relationships. Chem Med Chem, 2009, 4, 594-614.
30. a) Murata, T.; Shimada, M.; Sakakibera, S.; Yohino, T.; Masuda, T.; Shintani, T.; Sato, H.; Koriyama, Y.; Fukushima, K.; Nunami, N.; Yamauchi, M. Synthesis and structure-activity relationships of novel IKK-6 inhibitors. Part 3: Orally active anti-inflammatory agents. Bioorg. Med. Chem. Lett. 2004, 14, 4019-4022; b) Pinto, D. G.; Silva, A. M. S.; Cavaleiro, J. A. Synthesis of 3-(2-benzyloxy-6-hydroxyphenyl)-1-methylpyrazoles by the reaction of chromones with methylhydrazine. J. Heterocycl. Chem. 2000, 37, 1629-1634; c) Patil, A. D.; Deshpande, V. H. Indian J. Chem. Sect. B 1983, 22, 109-113.
31. Sang-Hun Jung, Soo-Hyun Cho, The Hung Dang, Jee-Hyun Lee, Jung-Hun Ju, Mi-Kyung Kim, Seung-Ho Lee, Jae-Chun Ryu, Youngsoo Kim. Structural requirement of isoflavonones for the inhibitory activity of interleukin-5. Eur. J. Med. Chem. 2003, 38, 537-545.
32. Owen, Sherry M., Rudolph, Donna L., Wang, W., Cole, A., Waring, A., Lal, R., Lehrer, R., RC-101, Retrocyclin-1 Analogue with Enhanced Activity against Primary HIV Type 1 Isolates, AIDS Research and Human Retroviruses, 2004, 20:11, 1157-1665.
33. Cole, Am., Yang, O., Warren, A., Waring, A., Lehrer, R., Cole, Al., HIV-1 Adapts to a Retrocyclin with Cationic Amino Acid Substitutions That Reduce Fusion Efficiency of gp41, Journal of Immunology, 2006, 176, 6900-6905.

It should be borne in mind that all patents, patent applications, patent publications, technical publications, scientific publications, and other references referenced herein and in the accompanying appendices are hereby incorporated by reference in this application to the extent not inconsistent with the teachings herein.

While various embodiments of the present invention have been shown and described herein, it will be obvious that such embodiments are provided by way of example only. Numerous variations, changes and substitutions may be made without departing from the invention herein. Accordingly, it is intended that the invention be limited only by the spirit and scope of the appended claims.

The invention claimed is:

1. A composition comprising a compound selected from the group consisting of 8c, 8d, 8f, 8h, 8i, 8j, 8k, 8l, 8m and combinations thereof;
   or pharmaceutically acceptable salt thereof.

2. The composition of claim 1, wherein the compound is at least one selected from the group consisting of 8l and 8m;
   or pharmaceutically acceptable salt thereof.

3. The composition of claim 1, wherein the compound is at least one selected from the group consisting of 8f, 8i, and 8m;
   or pharmaceutically acceptable salt thereof.

4. The composition of claim 1, further comprising a pharmaceutically acceptable carrier.

5. A US28 receptor modulator comprising a compound selected from the group consisting of 8c, 8d, 8f, 8h, 8i, 8j, 8k, 8l, 8m, and combinations thereof; or pharmaceutically acceptable salt thereof; and
   a pharmaceutically acceptable carrier.

6. The US28 receptor modulator of claim 5, wherein the compound is at least one selected from the group consisting of 8l and 8m;
   or pharmaceutically acceptable salt thereof.

7. The US28 receptor modulator of claim 5, wherein the compound is at least one selected from the group consisting of 8f, 8i, and 8m;
   or an analog, derivative, prodrug, stereoisomer, or pharmaceutically acceptable salt thereof.

8. A method for treating a disorder mediated by US28 receptor activity in a subject in need comprising administering to the subject an effective amount of a US receptor modulator comprising a compound selected from the group consisting of 8c, 8d, 8f, 8h, 8i, 8j, 8k, 8l, 8m, and combinations thereof.

9. The method of claim 8, wherein the disorder comprises a virus.

10. The method of claim 8, wherein the virus comprises a herpes virus.

11. The method of claim 8, wherein the virus comprises human cytomegalovirus (HCMV).

12. The method of claim 11, wherein the compound is at least one selected from the group consisting of 8f, 8i, and 8m.

13. The method of claim 8, wherein the virus comprises Human immunodeficiency virus (HIV).

14. The method of claim 13, wherein the compound is at least one selected from the group consisting of 8l and 8m.

15. The method of claim 8, wherein the disorder comprises one selected from the group consisting of a bacterial infection, acute inflammation, chronic inflammation, and a proliferative disorder.

16. A method for treating or preventing a virus infection in a subject comprising: administering to the subject an effective amount of a composition comprising a compound selected from the group consisting of 8c, 8d, 8f, 8h, 8i, 8j, 8k, 8l, 8m, and combinations thereof.

17. The method of claim 16, wherein the virus comprises a herpes virus.

18. The method of claim 16, wherein the virus comprises human cytomegalovirus (HCMV).

19. The method of claim 16, wherein the virus comprises Human immunodeficiency virus (HIV).

* * * * *